(12) United States Patent
Callaghan et al.

(10) Patent No.: US 8,764,848 B2
(45) Date of Patent: Jul. 1, 2014

(54) OCCLUDER DEVICE DOUBLE SECUREMENT SYSTEM FOR DELIVERY/RECOVERY OF SUCH OCCLUDER DEVICE

(75) Inventors: David J. Callaghan, Boston, MA (US); Noel McLellan, Boston, MA (US)

(73) Assignee: W.L. Gore & Associates, Inc., Flagstaff, AZ (US)

(*) Notice: Subject to any disclaimer, the term of this patent is extended or adjusted under 35 U.S.C. 154(b) by 1364 days.

(21) Appl. No.: 11/235,661

(22) Filed: Sep. 26, 2005

(65) Prior Publication Data

US 2006/0122647 A1 Jun. 8, 2006

Related U.S. Application Data

(60) Provisional application No. 60/612,857, filed on Sep. 24, 2004, provisional application No. 60/662,990, filed on Mar. 18, 2005, provisional application No. 60/663,289, filed on Mar. 18, 2005, provisional application No. 60/692,781, filed on Jun. 22, 2005.

(51) Int. Cl.
*A61F 2/02* (2006.01)

(52) U.S. Cl.
USPC ........................................... 623/23.72

(58) Field of Classification Search
CPC ................. A61B 17/0057; A61B 2017/00575
USPC ............ 623/23.72–23.74; 606/153, 157, 200, 606/213
See application file for complete search history.

(56) References Cited

U.S. PATENT DOCUMENTS

| | | |
|---|---|---|
| 3,874,388 A | 4/1975 | King et al. |
| 3,875,648 A | 4/1975 | Bone |

(Continued)

FOREIGN PATENT DOCUMENTS

| | | |
|---|---|---|
| DE | 94 13 645 U1 | 10/1994 |
| EP | 0 362 113 | 4/1990 |

(Continued)

OTHER PUBLICATIONS

Athanasion, T., "Coronary Artery Bypass with the Use of a Magnetic Distal Anastomotic Device: Surgical Technique and Preliminary Experience," The Heart Surgery Forum #2004-1024, 2004, 4 pgs.

(Continued)

*Primary Examiner* — Melanie Tyson
(74) *Attorney, Agent, or Firm* — DLA Piper LLP (US)

(57) ABSTRACT

Devices, delivery systems and delivery techniques for an occlusion device for the closure of physical anomalies, such as an atrial septal defect, a patent foramen ovale (PFO), and other septal and vascular defects are described. The devices, delivery systems and delivery techniques relate particularly to, but are not limited to, a patent foramen ovale (PFO) occluder made from a polymer tube. Specifically, a petal-shaped occluder with a catch system is provided within a delivery sheath. In certain embodiments, the delivery system includes a first securement system for securing a first end of the occluder and a second securement system for securing a second end of the occluder to a delivery catheter and a delivery wire contained in the delivery system. The securement enable the deployment (and retrieval) of the device. The securement systems enable pushing and pulling of respective ends of the occluder to expand and contract the device by varying its axial length. In one aspect, the first securement system employs a threaded connection and the second securement system employs a suture connection. In another aspect, the first securement system employs a threaded connection and the second securement system employs a collet finger connection. The securement systems are detached when the device has been properly positioned. The securement systems can be manipulated by control systems provided in the control portion of the delivery system.

5 Claims, 27 Drawing Sheets

(56) References Cited

U.S. PATENT DOCUMENTS

| | | |
|---|---|---|
| 3,924,631 A | 12/1975 | Mancusi |
| 4,006,747 A | 2/1977 | Kronenthal et al. |
| 4,007,743 A | 2/1977 | Blake |
| 4,425,908 A | 1/1984 | Simon |
| 4,610,674 A | 9/1986 | Suzuki et al. |
| 4,626,245 A | 12/1986 | Weinstein |
| 4,693,249 A | 9/1987 | Schenck et al. |
| 4,696,300 A | 9/1987 | Anderson |
| 4,710,181 A | 12/1987 | Fuqua |
| 4,710,192 A | 12/1987 | Liotta et al. |
| 4,738,666 A | 4/1988 | Fuqua |
| 4,836,204 A | 6/1989 | Landymore et al. |
| 4,840,623 A | 6/1989 | Quackenbush |
| 4,902,508 A | 2/1990 | Badylak et al. |
| 4,915,107 A | 4/1990 | Rebuffat et al. |
| 4,917,089 A | 4/1990 | Sideris |
| 4,921,479 A | 5/1990 | Grayzel |
| 4,956,178 A | 9/1990 | Badylak et al. |
| 5,021,059 A | 6/1991 | Kensey et al. |
| 5,037,433 A | 8/1991 | Wilk et al. |
| 5,041,129 A | 8/1991 | Hayhurst et al. |
| 5,049,131 A | 9/1991 | Deuss |
| 5,078,736 A | 1/1992 | Behl |
| 5,108,420 A | 4/1992 | Marks |
| 5,149,327 A | 9/1992 | Oshiyama |
| 5,163,131 A | 11/1992 | Row et al. |
| 5,167,637 A | 12/1992 | Okada et al. |
| 5,171,259 A | 12/1992 | Inoue |
| 5,176,659 A | 1/1993 | Mancini |
| 5,192,301 A | 3/1993 | Kamiya et al. |
| 5,222,974 A | 6/1993 | Kensey et al. |
| 5,226,879 A | 7/1993 | Ensminger et al. |
| 5,236,440 A | 8/1993 | Hlavacek |
| 5,245,023 A | 9/1993 | Peoples et al. |
| 5,257,637 A | 11/1993 | El Gazayerli |
| 5,275,826 A | 1/1994 | Badylak et al. |
| 5,282,827 A | 2/1994 | Kensey et al. |
| 5,284,488 A | 2/1994 | Sideris |
| 5,304,184 A | 4/1994 | Hathaway et al. |
| 5,312,341 A | 5/1994 | Turi |
| 5,312,435 A | 5/1994 | Nash et al. |
| 5,320,611 A | 6/1994 | Bonutti et al. |
| 5,334,217 A | 8/1994 | Das |
| 5,350,363 A | 9/1994 | Goode et al. |
| 5,354,308 A | 10/1994 | Simon et al. |
| 5,364,356 A | 11/1994 | Hofling |
| 5,411,481 A | 5/1995 | Allen et al. |
| 5,413,584 A | 5/1995 | Schulze |
| 5,417,699 A | 5/1995 | Klein et al. |
| 5,425,744 A | 6/1995 | Fagan et al. |
| 5,433,727 A | 7/1995 | Sideris |
| 5,451,235 A | 9/1995 | Lock et al. |
| 5,453,099 A | 9/1995 | Lee et al. |
| 5,478,353 A | 12/1995 | Yoon |
| 5,480,424 A | 1/1996 | Cox |
| 5,486,193 A | 1/1996 | Bourne et al. |
| 5,507,811 A | 4/1996 | Koike et al. |
| 5,540,712 A | 7/1996 | Kleshinski et al. |
| 5,562,632 A | 10/1996 | Davila et al. |
| 5,577,299 A | 11/1996 | Thompson et al. |
| 5,601,571 A | 2/1997 | Moss |
| 5,603,703 A | 2/1997 | Elsberry et al. |
| 5,618,311 A | 4/1997 | Gryskiewicz |
| 5,620,461 A | 4/1997 | Muijs Van De Moer et al. |
| 5,626,599 A | 5/1997 | Bourne et al. |
| 5,634,936 A | 6/1997 | Linden et al. |
| 5,649,950 A | 7/1997 | Bourne et al. |
| 5,663,063 A | 9/1997 | Peoples et al. |
| 5,683,411 A | 11/1997 | Kavteladze et al. |
| 5,690,674 A | 11/1997 | Diaz |
| 5,693,085 A | 12/1997 | Buirge et al. |
| 5,702,421 A | 12/1997 | Schneidt |
| 5,709,707 A | 1/1998 | Lock et al. |
| 5,713,864 A | 2/1998 | Verkaart |
| 5,720,754 A | 2/1998 | Middleman et al. |
| 5,725,552 A * | 3/1998 | Kotula et al. .................. 606/213 |
| 5,733,294 A | 3/1998 | Forber et al. |
| 5,733,337 A | 3/1998 | Carr, Jr. et al. |
| 5,741,297 A | 4/1998 | Simon |
| 5,772,641 A | 6/1998 | Wilson |
| 5,776,162 A | 7/1998 | Kleshinski |
| 5,776,183 A | 7/1998 | Kanesaka et al. |
| 5,797,960 A | 8/1998 | Stevens et al. |
| 5,800,516 A | 9/1998 | Fine et al. |
| 5,810,884 A | 9/1998 | Kim |
| 5,820,594 A | 10/1998 | Fontirroche et al. |
| 5,823,956 A | 10/1998 | Roth et al. |
| 5,829,447 A | 11/1998 | Stevens et al. |
| 5,853,420 A | 12/1998 | Chevillon et al. |
| 5,853,422 A | 12/1998 | Huebsch et al. |
| 5,855,614 A | 1/1999 | Stevens et al. |
| 5,861,003 A | 1/1999 | Latson et al. |
| 5,865,791 A | 2/1999 | Whayne et al. |
| 5,879,366 A | 3/1999 | Shaw et al. |
| 5,893,856 A | 4/1999 | Jacob et al. |
| 5,902,287 A | 5/1999 | Martin |
| 5,902,319 A | 5/1999 | Daley |
| 5,904,703 A | 5/1999 | Gilson |
| 5,919,200 A | 7/1999 | Stambaugh et al. |
| 5,924,424 A | 7/1999 | Stevens et al. |
| 5,928,250 A | 7/1999 | Koike et al. |
| 5,944,691 A | 8/1999 | Querns et al. |
| 5,944,738 A | 8/1999 | Amplatz et al. |
| 5,955,110 A | 9/1999 | Patel et al. |
| 5,976,174 A | 11/1999 | Ruiz |
| 5,980,505 A | 11/1999 | Wilson |
| 5,989,268 A | 11/1999 | Pugsley, Jr. et al. |
| 5,993,475 A | 11/1999 | Lin et al. |
| 5,993,844 A | 11/1999 | Abraham et al. |
| 5,997,575 A | 12/1999 | Whitson et al. |
| 6,010,517 A | 1/2000 | Baccaro |
| 6,019,753 A | 2/2000 | Pagan |
| 6,024,756 A | 2/2000 | Huebsch et al. |
| 6,027,519 A | 2/2000 | Stanford |
| 6,030,007 A | 2/2000 | Bassily et al. |
| 6,056,760 A | 5/2000 | Koike et al. |
| 6,071,998 A | 6/2000 | Muller et al. |
| 6,077,291 A | 6/2000 | Das |
| 6,077,880 A | 6/2000 | Castillo et al. |
| 6,079,414 A | 6/2000 | Roth |
| 6,080,182 A | 6/2000 | Shaw et al. |
| 6,096,347 A | 8/2000 | Gedees et al. |
| 6,106,913 A | 8/2000 | Scardino et al. |
| 6,113,609 A | 9/2000 | Adams |
| 6,117,159 A | 9/2000 | Buscemi et al. |
| 6,126,686 A | 10/2000 | Badylak et al. |
| 6,132,438 A | 10/2000 | Fleischman et al. |
| 6,143,037 A | 11/2000 | Goldstein et al. |
| 6,152,144 A | 11/2000 | Lesh et al. |
| 6,165,183 A | 12/2000 | Kuehn et al. |
| 6,165,204 A | 12/2000 | Levinson et al. |
| 6,168,588 B1 | 1/2001 | Wilson |
| 6,171,329 B1 | 1/2001 | Shaw et al. |
| 6,174,322 B1 | 1/2001 | Schneidt |
| 6,174,330 B1 | 1/2001 | Stinson |
| 6,183,443 B1 | 2/2001 | Kratoska et al. |
| 6,187,039 B1 | 2/2001 | Hiles et al. |
| 6,190,353 B1 | 2/2001 | Garibotto et al. |
| 6,190,357 B1 | 2/2001 | Ferrari et al. |
| 6,197,016 B1 | 3/2001 | Fourkas et al. |
| 6,199,262 B1 | 3/2001 | Martin |
| 6,206,895 B1 | 3/2001 | Levinson |
| 6,206,907 B1 | 3/2001 | Marino et al. |
| 6,214,029 B1 | 4/2001 | Thill et al. |
| 6,217,590 B1 | 4/2001 | Levinson |
| 6,221,092 B1 | 4/2001 | Koike et al. |
| 6,227,139 B1 | 5/2001 | Nguyen et al. |
| 6,228,097 B1 | 5/2001 | Levinson et al. |
| 6,231,561 B1 | 5/2001 | Frazier et al. |
| 6,245,080 B1 | 6/2001 | Levinson |
| 6,245,537 B1 | 6/2001 | Williams et al. |
| 6,261,309 B1 | 7/2001 | Urbanski |
| 6,265,333 B1 | 7/2001 | Dzenis et al. |
| 6,270,515 B1 | 8/2001 | Linden et al. |

(56) References Cited

U.S. PATENT DOCUMENTS

| | | |
|---|---|---|
| 6,277,138 B1 | 8/2001 | Levinson et al. |
| 6,277,139 B1 | 8/2001 | Levinson et al. |
| 6,287,317 B1 | 9/2001 | Makower et al. |
| 6,290,674 B1 | 9/2001 | Roue et al. |
| 6,299,635 B1 | 10/2001 | Frantzen |
| 6,306,150 B1 | 10/2001 | Levinson |
| 6,306,424 B1 | 10/2001 | Vyakarnam et al. |
| 6,312,443 B1 | 11/2001 | Stone |
| 6,312,446 B1 | 11/2001 | Huebsch et al. |
| 6,315,791 B1 | 11/2001 | Gingras et al. |
| 6,316,262 B1 | 11/2001 | Huisman et al. |
| 6,319,263 B1 | 11/2001 | Levinson |
| 6,322,548 B1 | 11/2001 | Payne et al. |
| 6,328,727 B1 | 12/2001 | Frazier et al. |
| 6,334,872 B1 | 1/2002 | Termin et al. |
| 6,342,064 B1 | 1/2002 | Koike et al. |
| 6,344,048 B1 | 2/2002 | Chin et al. |
| 6,344,049 B1 | 2/2002 | Levinson et al. |
| 6,346,074 B1 | 2/2002 | Roth |
| 6,348,041 B1 | 2/2002 | Klint |
| 6,352,552 B1 | 3/2002 | Levinson et al. |
| 6,355,052 B1 | 3/2002 | Neuss et al. |
| 6,356,782 B1 | 3/2002 | Sirimanne et al. |
| 6,358,238 B1 | 3/2002 | Sherry |
| 6,364,853 B1 | 4/2002 | French et al. |
| 6,371,904 B1 | 4/2002 | Sirimanne et al. |
| 6,375,625 B1 | 4/2002 | French et al. |
| 6,375,668 B1 * | 4/2002 | Gifford et al. ............... 606/200 |
| 6,375,671 B1 | 4/2002 | Kobayashi et al. |
| 6,379,342 B1 | 4/2002 | Levinson |
| 6,379,368 B1 | 4/2002 | Corcoran et al. |
| 6,387,104 B1 | 5/2002 | Pugsley, Jr. et al. |
| 6,398,796 B2 | 6/2002 | Levinson |
| 6,402,772 B1 | 6/2002 | Amplatz et al. |
| 6,419,669 B1 | 7/2002 | Van Der Burg et al. |
| 6,426,145 B1 | 7/2002 | Moroni |
| 6,436,088 B2 | 8/2002 | Frazier et al. |
| 6,440,152 B1 | 8/2002 | Gainor et al. |
| 6,450,987 B1 | 9/2002 | Kramer |
| 6,460,749 B1 | 10/2002 | Levinson et al. |
| 6,482,224 B1 | 11/2002 | Michler et al. |
| 6,488,706 B1 | 12/2002 | Solymar |
| 6,494,846 B1 | 12/2002 | Margolis |
| 6,494,888 B1 | 12/2002 | Laufer et al. |
| 6,508,828 B1 | 1/2003 | Akerfeldt et al. |
| 6,514,515 B1 | 2/2003 | Williams |
| 6,548,569 B1 | 4/2003 | Williams et al. |
| 6,551,303 B1 | 4/2003 | Van Tassel et al. |
| 6,551,344 B2 | 4/2003 | Thill |
| 6,585,719 B2 | 7/2003 | Wang |
| 6,585,755 B2 | 7/2003 | Jackson et al. |
| 6,596,013 B2 | 7/2003 | Yang et al. |
| 6,599,448 B1 | 7/2003 | Ehrhard, Jr. et al. |
| 6,610,764 B1 | 8/2003 | Martin et al. |
| 6,623,508 B2 | 9/2003 | Shaw et al. |
| 6,623,518 B2 | 9/2003 | Thompson et al. |
| 6,626,936 B2 | 9/2003 | Stinson |
| 6,629,901 B2 | 10/2003 | Huang |
| 6,666,861 B1 | 12/2003 | Grabek |
| 6,669,722 B2 | 12/2003 | Chen et al. |
| 6,689,589 B2 | 2/2004 | Huisman et al. |
| 6,712,804 B2 | 3/2004 | Roue et al. |
| 6,712,836 B1 | 3/2004 | Berg et al. |
| 6,726,696 B1 | 4/2004 | Houser et al. |
| 6,828,357 B1 | 12/2004 | Martin et al. |
| 6,838,493 B2 | 1/2005 | Williams et al. |
| 6,867,247 B2 | 3/2005 | Williams et al. |
| 6,867,248 B1 | 3/2005 | Martin et al. |
| 6,921,410 B2 | 7/2005 | Porter |
| 8,118,833 B2 * | 2/2012 | Seibold et al. ............... 606/215 |
| 2001/0014800 A1 | 8/2001 | Frazier et al. |
| 2001/0025132 A1 | 9/2001 | Alferness et al. |
| 2001/0034537 A1 | 10/2001 | Shaw et al. |
| 2001/0037129 A1 | 11/2001 | Thill |
| 2001/0039435 A1 | 11/2001 | Roue et al. |
| 2001/0039436 A1 | 11/2001 | Frazier et al. |
| 2001/0041914 A1 | 11/2001 | Frazier et al. |
| 2001/0041915 A1 | 11/2001 | Roue et al. |
| 2001/0044639 A1 | 11/2001 | Levinson |
| 2001/0049492 A1 | 12/2001 | Frazier et al. |
| 2002/0010481 A1 | 1/2002 | Jayaraman |
| 2002/0019648 A1 | 2/2002 | Akerfeldt et al. |
| 2002/0022859 A1 | 2/2002 | Hogendijk |
| 2002/0022860 A1 | 2/2002 | Borillo et al. |
| 2002/0026208 A1 | 2/2002 | Roe et al. |
| 2002/0029048 A1 | 3/2002 | Miller |
| 2002/0032459 A1 | 3/2002 | Horzewski et al. |
| 2002/0032462 A1 | 3/2002 | Houser et al. |
| 2002/0035374 A1 | 3/2002 | Borillo et al. |
| 2002/0043307 A1 | 4/2002 | Ishida et al. |
| 2002/0049457 A1 | 4/2002 | Kaplan et al. |
| 2002/0052572 A1 | 5/2002 | Franco et al. |
| 2002/0058989 A1 | 5/2002 | Chen et al. |
| 2002/0077555 A1 | 6/2002 | Schwartz |
| 2002/0095174 A1 | 7/2002 | Tsugita et al. |
| 2002/0096183 A1 | 7/2002 | Stevens et al. |
| 2002/0099389 A1 | 7/2002 | Michler et al. |
| 2002/0099390 A1 | 7/2002 | Kaplan et al. |
| 2002/0103492 A1 | 8/2002 | Kaplan et al. |
| 2002/0107531 A1 | 8/2002 | Schreck et al. |
| 2002/0111637 A1 | 8/2002 | Kaplan et al. |
| 2002/0111647 A1 | 8/2002 | Khairkhahan et al. |
| 2002/0120323 A1 | 8/2002 | Thompson et al. |
| 2002/0128680 A1 | 9/2002 | Pavlovic |
| 2002/0129819 A1 | 9/2002 | Feldman et al. |
| 2002/0164729 A1 | 11/2002 | Skraly et al. |
| 2002/0169377 A1 | 11/2002 | Khairkhahan et al. |
| 2002/0183786 A1 | 12/2002 | Girton |
| 2002/0183787 A1 | 12/2002 | Wahr et al. |
| 2002/0183823 A1 | 12/2002 | Pappu |
| 2002/0198563 A1 | 12/2002 | Gainor |
| 2003/0004533 A1 | 1/2003 | Dieck et al. |
| 2003/0028213 A1 | 2/2003 | Thill et al. |
| 2003/0045893 A1 | 3/2003 | Ginn |
| 2003/0050665 A1 | 3/2003 | Ginn |
| 2003/0055455 A1 | 3/2003 | Yang et al. |
| 2003/0059640 A1 | 3/2003 | Marton et al. |
| 2003/0065379 A1 | 4/2003 | Babbas et al. |
| 2003/0100920 A1 | 5/2003 | Akin et al. |
| 2003/0139819 A1 | 7/2003 | Beer et al. |
| 2003/0171774 A1 * | 9/2003 | Freudenthal et al. ......... 606/213 |
| 2003/0191495 A1 | 10/2003 | Ryan et al. |
| 2003/0195530 A1 | 10/2003 | Thill |
| 2003/0204203 A1 | 10/2003 | Khairkhahan et al. |
| 2004/0044361 A1 | 3/2004 | Franzier et al. |
| 2004/0073242 A1 | 4/2004 | Chanduszko |
| 2004/0133236 A1 | 7/2004 | Chanduszko |
| 2004/0176799 A1 | 9/2004 | Chanduszko et al. |
| 2004/0210301 A1 | 10/2004 | Obermiller |
| 2004/0234567 A1 | 11/2004 | Dawson |
| 2005/0025809 A1 | 2/2005 | Hasirci et al. |
| 2005/0043759 A1 | 2/2005 | Chanduszko |
| 2005/0113868 A1 | 5/2005 | Devellian et al. |
| 2005/0267523 A1 | 12/2005 | Devellian et al. |
| 2005/0273135 A1 | 12/2005 | Chanduszko et al. |
| 2005/0288786 A1 | 12/2005 | Chanduszko |
| 2006/0122647 A1 | 6/2006 | Callaghan et al. |
| 2006/0265004 A1 | 11/2006 | Callaghan et al. |
| 2006/0271089 A1 | 11/2006 | Alejandro et al. |
| 2007/0010851 A1 | 1/2007 | Chanduszko et al. |
| 2007/0167981 A1 | 7/2007 | Opolski |

FOREIGN PATENT DOCUMENTS

| | | |
|---|---|---|
| EP | 0 474 887 | 3/1992 |
| EP | 0 839 549 A | 5/1998 |
| EP | 0 861 632 | 9/1998 |
| EP | 1 013 227 A2 | 6/2000 |
| EP | 1 046 375 | 10/2000 |
| EP | 1 222 897 | 7/2002 |
| WO | WO-96/25179 | 8/1996 |
| WO | WO-96/31157 | 10/1996 |
| WO | WO-98/07375 A1 | 2/1998 |
| WO | WO-98/08462 | 3/1998 |

(56) References Cited

FOREIGN PATENT DOCUMENTS

| | | |
|---|---|---|
| WO | WO-98/16174 | 4/1998 |
| WO | WO-98/29026 A | 7/1998 |
| WO | WO-98/51812 | 11/1998 |
| WO | WO-99/05977 A1 | 2/1999 |
| WO | WO-99/18862 A1 | 4/1999 |
| WO | WO-99/18864 | 4/1999 |
| WO | WO-99/18864 A1 | 4/1999 |
| WO | WO-99/18870 A1 | 4/1999 |
| WO | WO-99/18871 A1 | 4/1999 |
| WO | WO-99/30640 | 6/1999 |
| WO | WO-99/66846 | 12/1999 |
| WO | WO-00/27292 | 5/2000 |
| WO | WO-00/44428 | 8/2000 |
| WO | WO-01/08600 | 2/2001 |
| WO | WO-01/19256 | 3/2001 |
| WO | WO-01/21247 A1 | 3/2001 |
| WO | WO-01/28432 | 4/2001 |
| WO | WO-01/30268 A1 | 5/2001 |
| WO | WO-01/49185 | 7/2001 |
| WO | WO-01/78596 A1 | 10/2001 |
| WO | WO-01-93783 | 12/2001 |
| WO | WO-02/17809 A1 | 3/2002 |
| WO | WO-02/24106 | 3/2002 |
| WO | WO-03/024337 | 3/2003 |
| WO | WO-03/053493 | 7/2003 |
| WO | WO-03/059152 | 7/2003 |
| WO | WO-03/077733 | 9/2003 |
| WO | WO-03/082076 | 10/2003 |
| WO | WO-03/103476 | 12/2003 |
| WO | WO-2004/032993 | 4/2004 |
| WO | WO-2004/037333 | 5/2004 |
| WO | WO-2004/043266 | 5/2004 |
| WO | WO-2004/043508 | 5/2004 |
| WO | WO-2004/052213 | 6/2004 |
| WO | WO-2005/006990 | 1/2005 |
| WO | WO-2005/018728 | 3/2005 |
| WO | WO-2005/027752 | 3/2005 |
| WO | WO-2005/074813 | 8/2005 |
| WO | WO-2005/092203 | 10/2005 |
| WO | WO-2005/110240 | 11/2005 |
| WO | WO-2005/112779 | 12/2005 |
| WO | WO-2006/036837 | 4/2006 |
| WO | WO-2006/102213 | 9/2006 |

OTHER PUBLICATIONS

Bachthaler, M. et al., "Corrosion of Tungsten Coils After Peripheral Vascular Embolization Theraphy: Influence on Outcome and Tungsten Load", *Catherization and Cardiovascular Interventions*, vol. 62, pp. 380-384, 2004.

European Examination Report, European Application No. 04781644.2, mailed Aug. 23, 2007 (3 Pages).

Falk, V., "Facilitated Endoscopic Beating Heart Coronary Artery Bypass Grafting Using a Magentic Coupling Device," Journal of Thoracic and Cardiovascular Surgery, vol. 126,(5), pp. 1575-1579.

Filsoufi, F., et al., "Automated Distal Coronary Bypass with a Novel Magnetic Coupler (MVP system)," J. Thoracic and Cardiovascular Surgery, vol. 127(1), pp. 185-192.

International Search Report, International Application No. PCT/US02/40850 mailed Jun. 19, 2003 (4 pgs).

International Search Report, International Application No. PCT/US03/01050, mailed Jul. 8, 2003 (1 pg).

International Search Report, International Application No. PCT/US03/09051, mailed Sep. 29, 2003 (2 pgs).

International Search Report, International Application No. PCT/US03/17715, mailed Mar. 24, 2004 (2 pgs).

International Search Report, International Application No. PCT/US03/32133, mailed Apr. 22, 2004 (1 pg).

International Search Report, International Application No. PCT/US03/34003 mailed Oct. 3, 2004 (4 pgs).

International Search Report, International Application No. PCT/US03/35479, mailed Apr. 14, 2004 (2 pgs).

International Search Report, International Application No. PCT/US03/35998 mailed Jun. 16, 2004 (4 pgs).

International Search Report, International Application No. PCT/US03/39253, mailed Apr. 19, 2004 (4 pgs).

International Search Report, International Application No. PCT/US04/022643, mailed Mar. 31, 2005 (2 pgs).

International Search Report, International Application No. PCT/US04/026998, mailed Apr. 22, 2005 (5 pgs).

International Search Report, International Application No. PCT/US04/029978, mailed Jan. 26, 2005 (3 pgs).

International Search Report, International Application No. PCT/US05/006703, mailed Jul. 25, 2005 (3 pgs).

International Search Report, International Application No. PCT/US05/013705 mailed Aug. 4, 2005 (4 pgs).

International Search Report, International Application No. PCT/US05/015382, mailed Oct. 6, 2005 (4 pgs).

International Search Report, International Application No. PCT/US05/34276, mailed 9 Oct. 2007 (3 pgs).

International Search Report, International Application No. PCT/US06/009978, mailed Jul. 13, 2006 (2 pgs).

International Search Report, International Application No. PCT/US2007/065526, mailed Aug. 8, 2007 (5 pgs).

International Search Report, International Application No. PCT/US2007/065541, mailed Aug. 7, 2007 (3 pgs).

International Search Report, International Application No. PCT/US97/14822, mailed Feb. 20, 1998 (2 pgs).

International Search Report, International Application No. PCT/US97/17927, mailed Feb. 10, 1998 (1 pg).

Isotalo, T. et al., "Biocompatibility Testing of a New Bioabsorbable X-Ray Positive SR-PLA 96/4 Urethral Stent", *The Journal of Urology*, vol. 163, pp. 1764-1767, Nov. 1999.

Klima, U., "Magnetic Vascular Port in Minimally Invasive Direct Coronary Artery Bypass Grafting," Circulation, 2004, II-55-II-60.

Parviainen, M. et al., "A New Biodegradable Stent for the Pancreaticojejunal Anastomosis After Pancreaticoduodenal Resection: In Vitro Examination and Pilot Experiences in Humans", *Pancreas*, vol. 21, No. 1, pp. 14-21, 2000.

Ruddy, A.C. et al., "Rheological, Mechanical and Thermal Behaviour of Radipaque Filled Polymers", *Polymer Processing Research Centre, School of Chemical Engineering, Queen's University of Belfast*, 5 pages.

Vaajanen, A. et al., "Expansion and Fixation Properties of a New Braided Biodegradable Urethral Stent: An Experimental Study in the Rabbit", *The Journal of Urology*, vol. 169, pp. 1771-1174, Mar. 2003.

European Examination Report, European Application No. 03729663.9, mailed Jul. 16, 2008 (5 Pages).

European Examination Report, European Application No. 03731562.9, mailed Jul. 18, 2008 (3 Pages).

European Examination Report, European Application No. 03779297.5, mailed Mar. 15, 2007 (6 Pages).

European Search Report, European Application No. 03729663.9, mailed Feb. 20, 2008 (3 Pages).

International Search Report and Written Opinion, International Patent Application No. PCT/US06/41255, mailed Jun. 13, 2008 (6 pgs).

International Search Report and Written Opinion, International Patent Application No. PCT/US08/59429, mailed Sep. 5, 2008 (9 pgs).

International Search Report for International Patent Application No. PCT/AU03/00759, filed Jun. 19, 2003.

International Search Report, International Application No. PCT/US07/065546, mailed Oct. 29, 2007. 4 pages.

International Search Report, International Application No. PCT/US03/17390, mailed Oct. 6, 2003 (4 pgs).

Kimura, A., et al., "Effects of Neutron Irradiation on the Transformation Behavior in Ti-Ni Alloys," Abstract, Proceedings of the Int'l Conf. on Mariensitic Transformations, 1992, pp. 935-940.

Meier, MD, Bernhard et al., "Contemporary Management of Patent Foramen Ovale," American Heart Association, Inc., Circulation, 2003, vol. 107, pp. 5-9.

(56) References Cited

OTHER PUBLICATIONS

Nat'l Aeronautics and Space Administration, "55-Nitinol—The Alloy with a Memory: Its Physical Metallurgy, Properties and Applications," NASA Report, pp. 24-25.

Ramanathan, G., et al., "Experimental and Computational Methods for Shape Memory Alloys," 15th ASCE Engineering Mechanics Conference, Jun. 2-5, 2002.

Ruiz, et al, "The Puncture Technique: A New Method for Transcatheter Closure of Patent Foramen Ovale," Catheterization and Cardiovascular Interventions, 2001, vol. 53, pp. 369-372.

Shabalovskaya, S., "Surface, Corrosion and Biocompatibility Aspects of Nitinol as an Implant Material," Bio-Medical Materials and Engineering, 2002, vol. 12, pp. 69-109.

SMST-2000, "Proceedings of the International Conference on Shape Memory and Superelastic Technologies," Apr. 30 to May 4, 2000, Asilomar Conference Center.

Stockel, "Nitinol Medical Devices and Implants," SMST-2000 Conference Proceedings, 2001, pp. 531-541.

Uchil, J., "Shape Memory Alloys—Characterization Techniques," Pramana—Journal of Physics, 2002, vol. 58(5)(6), pp. 1131-1139.

\* cited by examiner

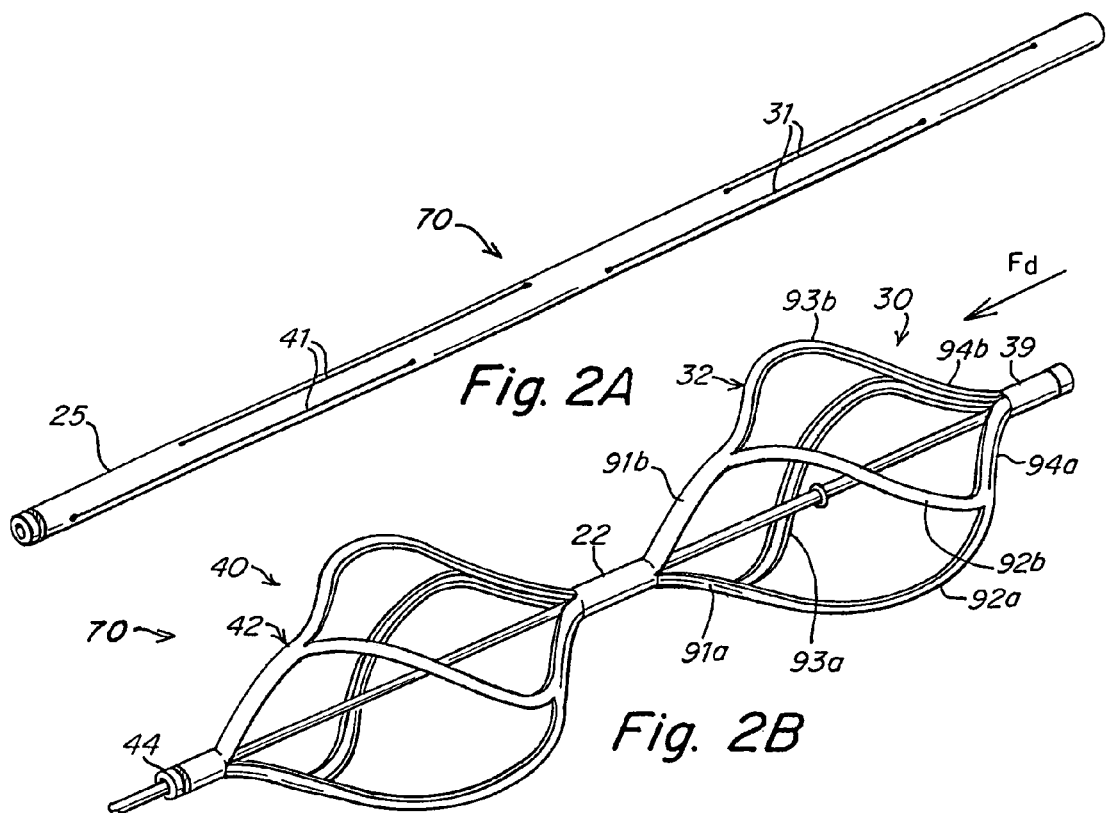
Fig. 2A
Fig. 2B
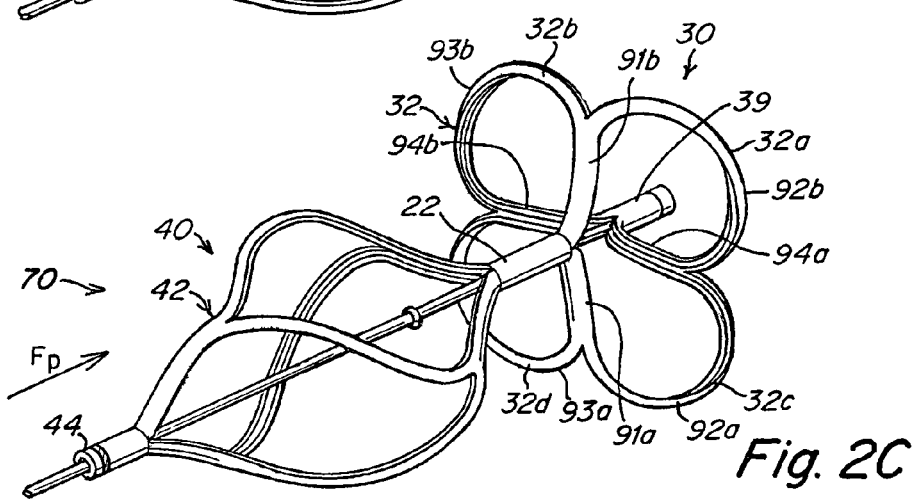
Fig. 2C
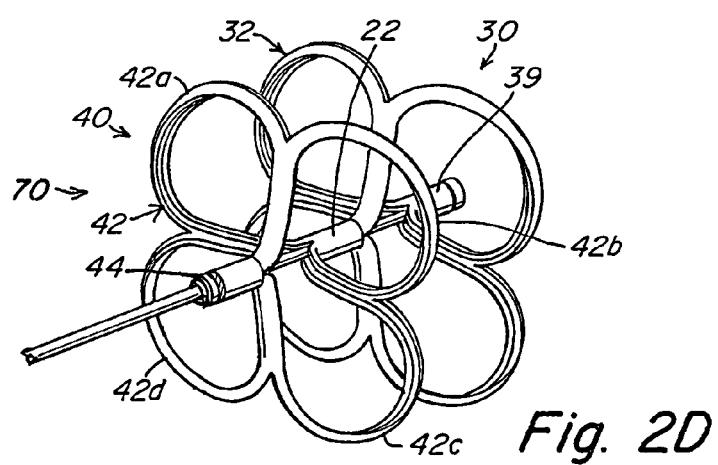
Fig. 2D

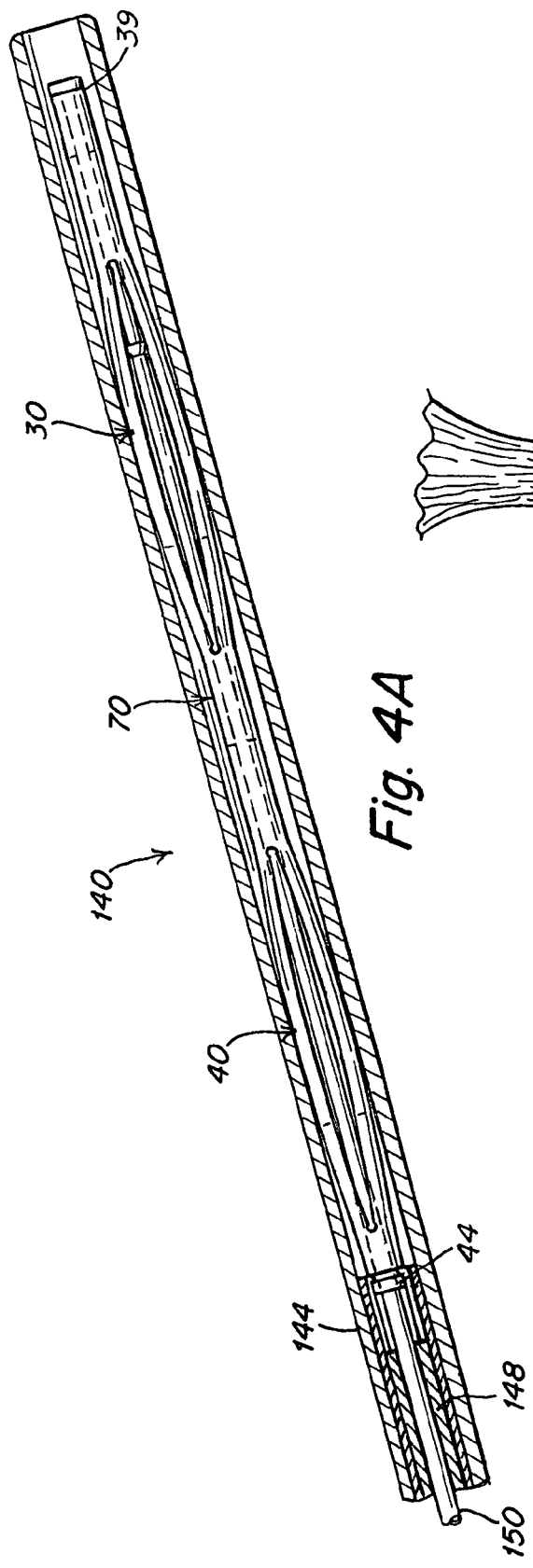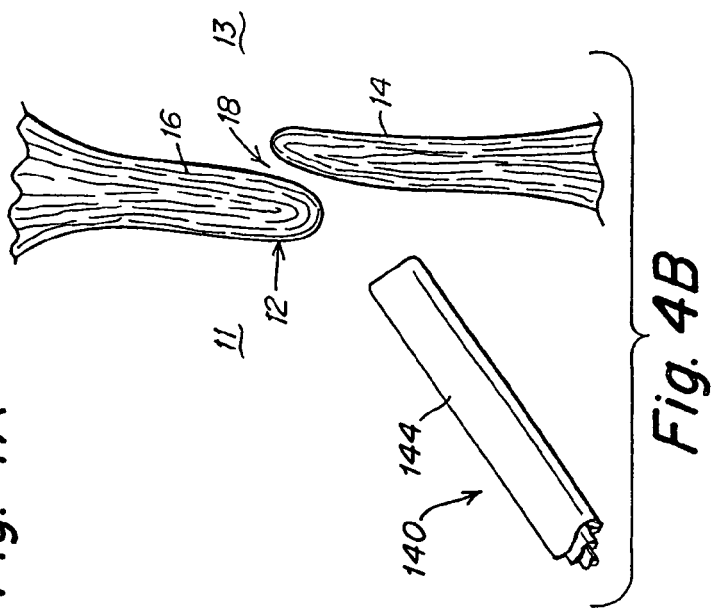

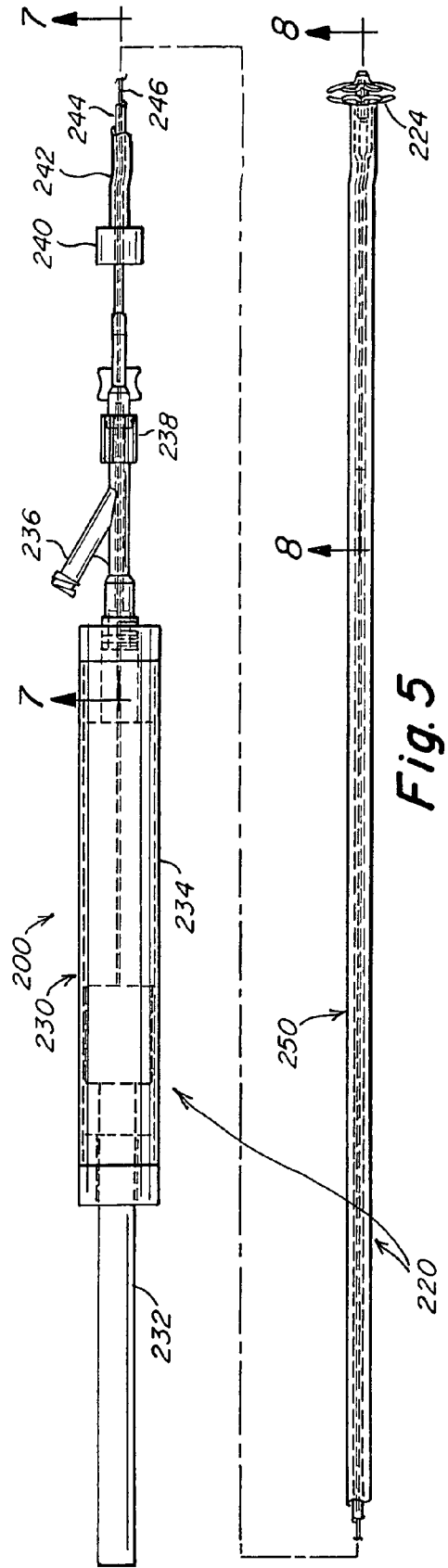
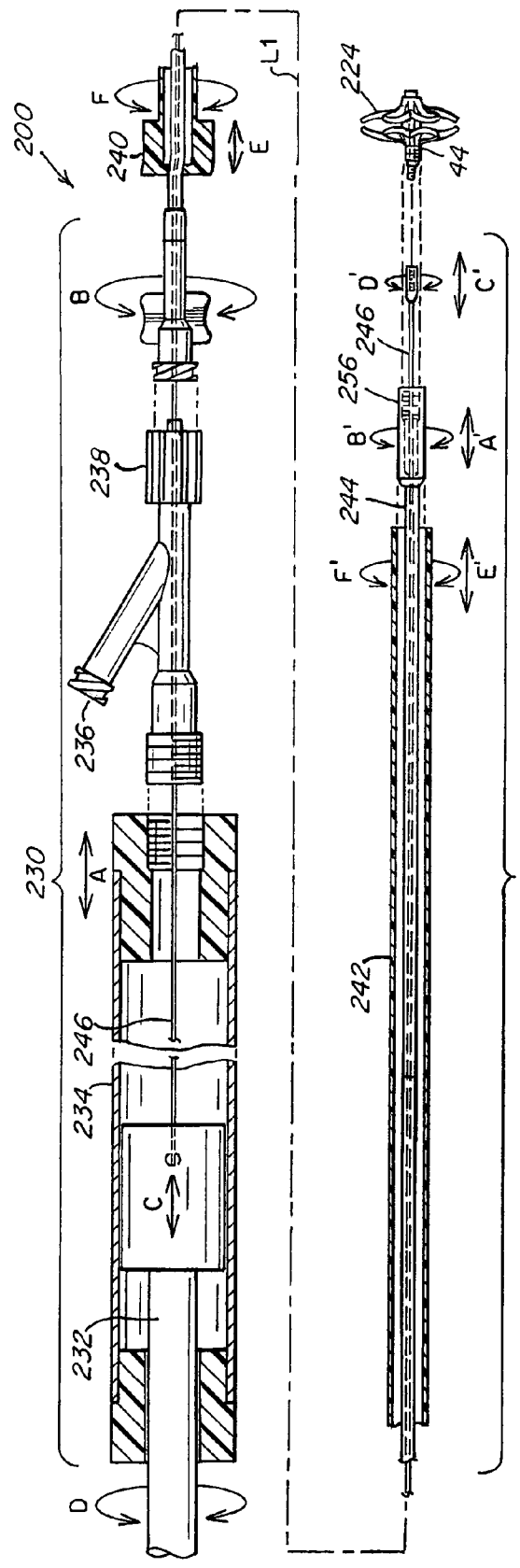
Fig. 5
Fig. 6

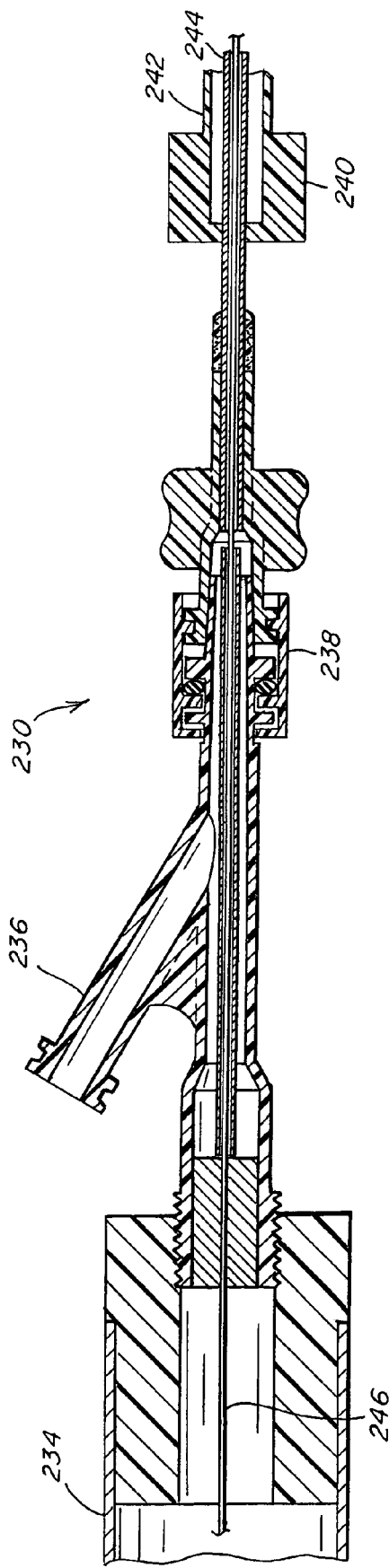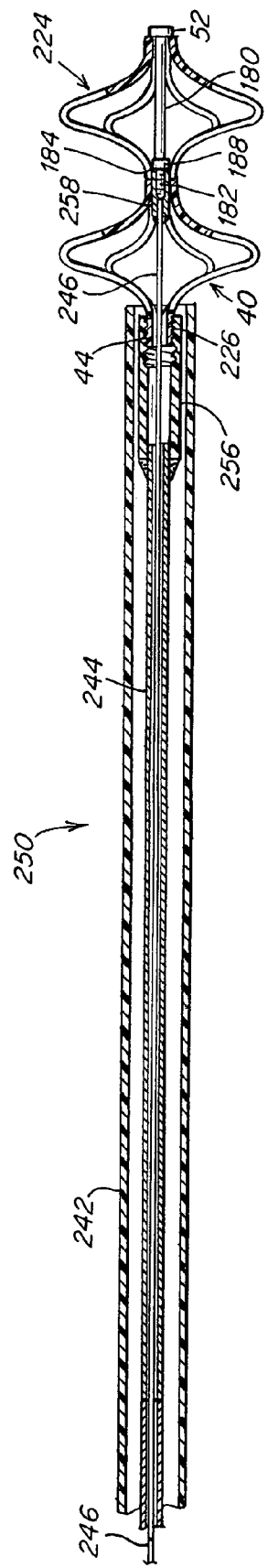

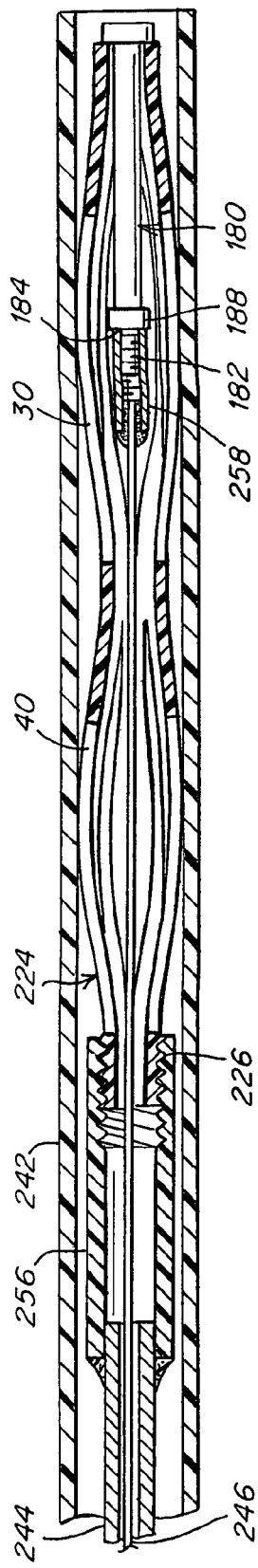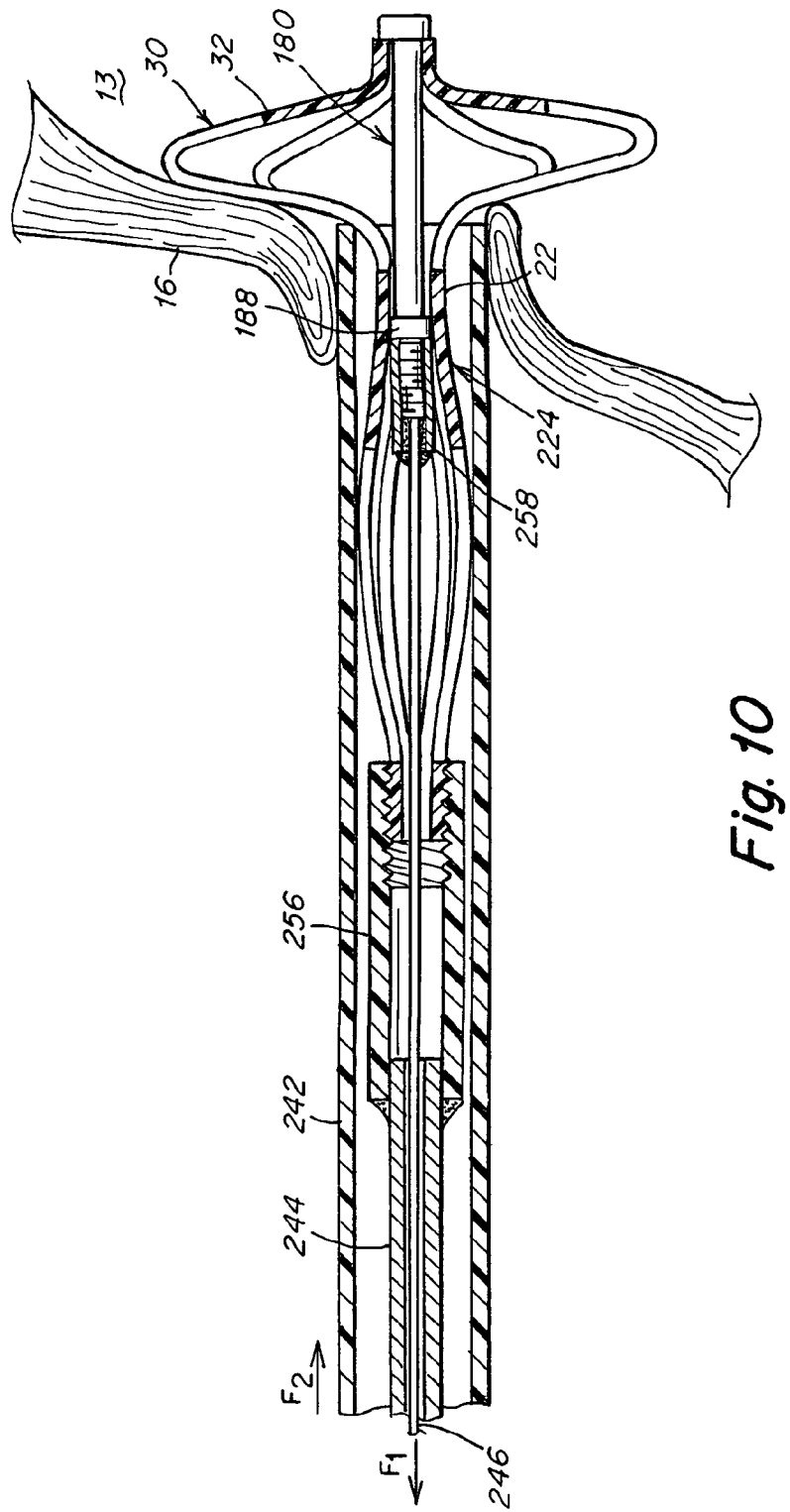

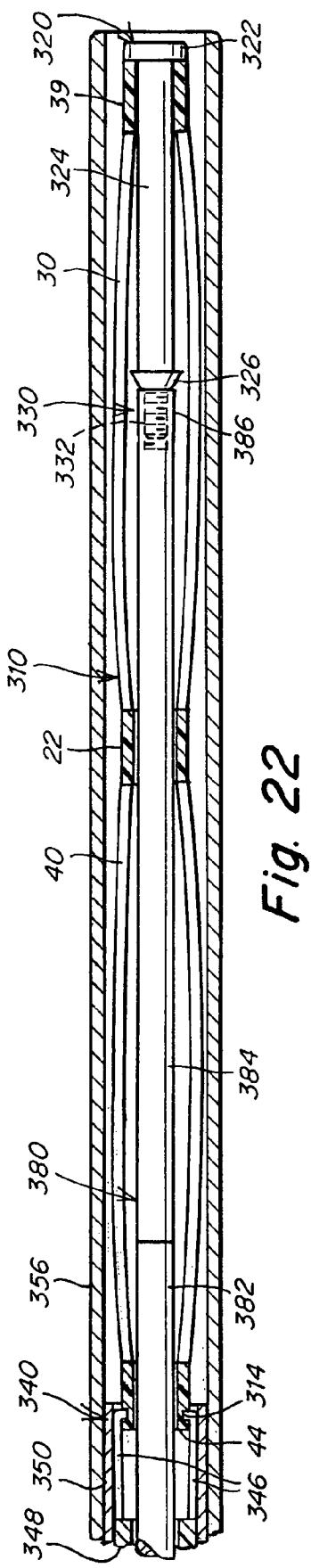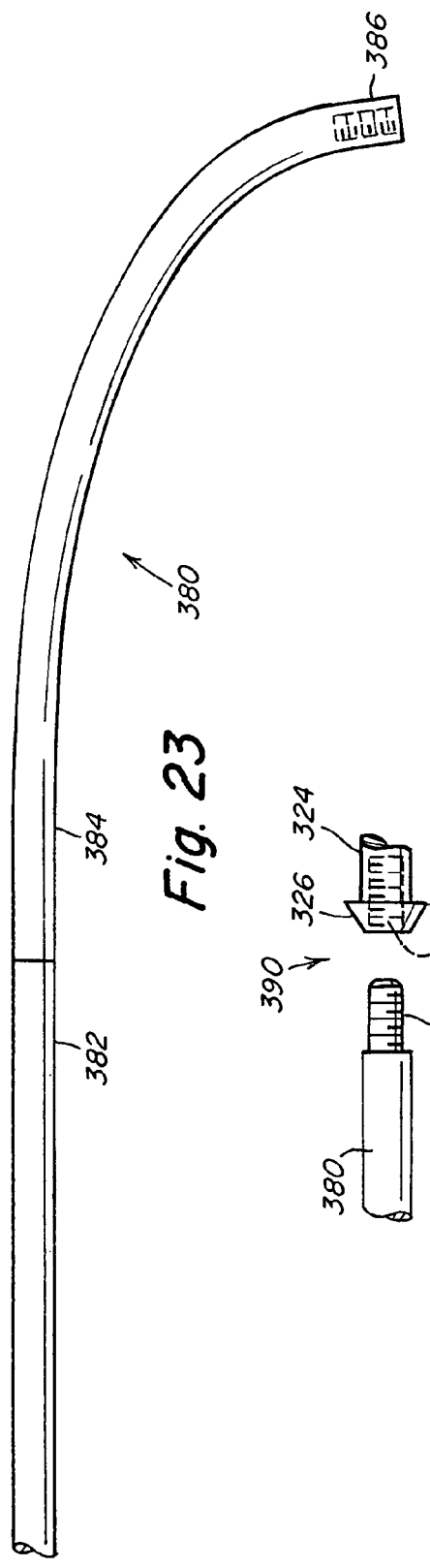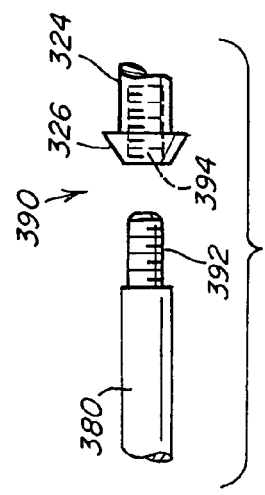
Fig. 22
Fig. 23
Fig. 24

OCCLUDER DEVICE DOUBLE SECUREMENT SYSTEM FOR DELIVERY/RECOVERY OF SUCH OCCLUDER DEVICE

RELATED APPLICATIONS

This application claims the benefit of priority to U.S. Provisional Application No. 60/612,857, filed Sep. 24, 2004, U.S. Provisional Application No. 60/662,990, filed Mar. 18, 2005, U.S. Provisional Application No. 60/663,289, filed Mar. 18, 2005, and U.S. Provisional Application No. 60/692,781, filed Jun. 22, 2005, the disclosures of each of which are incorporated by reference herein.

TECHNICAL FIELD

This invention relates generally to occlusion devices for the closure of physical anomalies, such as an atrial septal defect, a patent foramen ovale, and other septal and vascular defects. The invention also relates to delivery systems and mechanisms for such devices.

BACKGROUND

A patent foramen ovale (PFO), illustrated in FIG. 1, is a persistent, one-way, usually flap-like opening in the wall between the right atrium 11 and left atrium 13 of the heart 10. Because left atrial (LA) pressure is normally higher than right atrial (RA) pressure, the flap usually stays closed. Under certain conditions, however, right atrial pressure can exceed left atrial pressure, creating the possibility that blood could pass from the right atrium 11 to the left atrium 13 and blood clots could enter the systemic circulation. It is desirable that this circumstance be eliminated.

The foramen ovale serves a desired purpose when a fetus is gestating. Because blood is oxygenated through the umbilical cord, and not through the developing lungs, the circulatory system of the fetal heart allows the blood to flow through the foramen ovale as a physiologic conduit for right-to-left shunting. After birth, with the establishment of pulmonary circulation, the increased left atrial blood flow and pressure results in functional closure of the foramen ovale. This functional closure is subsequently followed by anatomical closure of the two over-lapping layers of tissue: septum primum 14 and septum secundum 16. However, a PFO has been shown to persist in a number of adults.

The presence of a PFO is generally considered to have no therapeutic consequence in otherwise healthy adults. Paradoxical embolism via a PFO is considered in the diagnosis for patients who have suffered a stroke or transient ischemic attack (TIA) in the presence of a PFO and without another identified cause of ischemic stroke. While there is currently no definitive proof of a cause-effect relationship, many studies have confirmed a strong association between the presence of a PFO and the risk for paradoxical embolism or stroke. In addition, there is significant evidence that patients with a PFO who have had a cerebral vascular event are at increased risk for future, recurrent cerebrovascular events.

Accordingly, patients at such an increased risk are considered for prophylactic medical therapy to reduce the risk of a recurrent embolic event. These patients are commonly treated with oral anticoagulants, which potentially have adverse side effects, such as hemorrhaging, hematoma, and interactions with a variety of other drugs. The use of these drugs can alter a person's recovery and necessitate adjustments in a person's daily living pattern.

In certain cases, such as when anticoagulation is contraindicated, surgery may be necessary or desirable to close a PFO. The surgery would typically include suturing a PFO closed by attaching septum secundum to septum primum. This sutured attachment can be accomplished using either an interrupted or a continuous stitch and is a common way a surgeon shuts a PFO under direct visualization.

Umbrella devices and a variety of other similar mechanical closure devices, developed initially for percutaneous closure of atrial septal defects (ASDs), have been used in some instances to close PFOs. These devices potentially allow patients to avoid the side effects often associated with anticoagulation therapies and the risks of invasive surgery. However, umbrella devices and the like that are designed for ASDs are not optimally suited for use as PFO closure devices.

Currently available septal closure devices present drawbacks, including technically complex implantation procedures. Additionally, there are significant complications due to thrombus, fractures of the components, conduction system disturbances, perforations of heart tissue, and residual leaks. Many devices have high septal profile and include large masses of foreign material, which may lead to unfavorable body adaptation of a device. Given that ASD devices are designed to occlude holes, many lack anatomic conformability to the flap-like anatomy of PFOs. Thus, when inserting an ASD device to close a PFO, the narrow opening and the thin flap may form impediments to proper deployment. Even if an occlusive seal is formed, the device may be deployed in the heart on an angle, leaving some components insecurely seated against the septum and, thereby, risking thrombus formation due to hemodynamic disturbances. Finally, some septal closure devices are complex to manufacture, which may result in inconsistent product performance.

Various delivery systems have been used to deliver occluders and other medical devices through body lumens. Some delivery systems of the prior art are used to deliver devices that readily expand to a delivered configuration when removed from the delivery system. Such delivery systems are not generally suited for delivering a device that does not readily expand into the delivered configuration. Further, the delivery systems of the prior art may not allow verification of the position of the device prior to full deployment of the device. Finally delivery systems of the prior art may not be suitable to manipulate the configuration of the device in a secure manner to allow for complete deployment of the device.

The devices and techniques disclosed herein are designed to address these and other deficiencies of prior art septal closure devices and techniques for delivering and retrieving such devices.

SUMMARY OF THE INVENTION

These and other aspects and embodiments of the disclosure are illustrated and described below.

This description discloses several delivery devices and techniques for delivering an implant into a desired location within the body. This delivery technique relates particularly to, but is not limited to, a septal occluder made from a polymer tube. These delivery techniques, in addition to use with septal occluders, could be applied to other medical devices, such as other expandable devices constructed from an underlying tubular structure.

In one aspect, a delivery system is disclosed for delivering an occluder that closes an aperture in septal tissue. The occluder includes a first side adapted to be disposed on one side of the septal tissue and a second side adapted to be disposed on the opposite side of the septal tissue. The first and second sides are adapted to occlude the aperture upon deployment of the device at its intended delivery location. The device also includes a catch system that maintains the configuration of the device once it has been deployed.

According to at least some embodiments, the device is formed from a tube. According to some embodiments, the tube includes a material selected from the group consisting of metals, shape memory materials, alloys, polymers, bioabsorbable polymers, and combinations thereof. In particular embodiments, the tube includes a shape memory polymer. In particular embodiments, the tube includes nitinol. In some embodiments, the tube is formed by rolling a flat piece of material into a tubular form. According to some embodiments, the device is formed by cutting the tube. The device is placed in its deployment configuration by reducing the axial length of the device.

According to some embodiments, the catch system reduces and maintains the axial length of the device. Also, varied constructions could be used to maintain the axial dimension of the device. In one form, catch elements such as, for example, balls, attached to a delivery wire could be used to maintain the axial dimension of the device. In a different construction, a locking mechanism could be used. Preferably, if a locking mechanism is used, it secures both sides of the device in the locked position with a single locking element. In some embodiments, a catch element secures the ends of the occluder in a compressed position. Preferably, if a catch mechanism is used, it secures both sides of the device in the deployed position with a single element.

In another aspect, the present invention provides a device for occluding an aperture in septal tissue, including a first side adapted to be disposed on one side of the septal tissue and a second side adapted to be disposed on the opposite side of the septal tissue. The first and second sides are adapted to occlude the defect when the device is deployed at its intended delivery location. Each of the first and second sides includes loops. The device further includes a catch system that maintains the configuration of the device once it has been deployed. The loops of the first and second sides and the catch system cooperate to provide a compressive force to the septal tissue surrounding the aperture.

According to some embodiments, each of the first and second sides includes at least two loops. In particular embodiments, each of the first and second sides includes four or six loops. Of course, the most desirable number of loops on each side will depend on a variety of anatomical and manufacturing factors. According to some embodiments, the device also includes a central tube that connects the first and second sides.

The delivery system may be used to deliver an occluder in which at least one of the first and second sides further includes a tissue scaffold. The tissue scaffold includes a material selected from the group consisting of polyester fabrics, Teflon-based materials, polyurethanes, metals, polyvinyl alcohol (PVA), extracellular matrix (ECM) or other bioengineered materials, synthetic bioabsorbable polymeric scaffolds, collagen, and combinations thereof. In particular embodiments, the tissue scaffold includes nitinol.

The delivery system includes a first and a second securement system. The first securement system may be any one of a number of configurations. First, a delivery wire may be used to secure the distal end of the occluder onto the delivery system. When a delivery wire is used, the distal end of the delivery wire may be threaded and cooperate with a corresponding threaded portion on the occluder. In a preferred form, the threaded portion may have male threads on the occluder and female threads on the delivery wire. Alternatively, a ball and clasp, other interlocking system may be used.

The second securement system may be any one of a number of configurations. In one aspect it may be a threaded connection between the delivery system and the occluder. In another aspect, the second securement system is a collet system that includes fingers, which are configured to fit within a groove in the occluder and thus secure the occluder to the delivery system when the fingers are disposed in the groove. A collet sheath is moveable with respect to the fingers and when the collet fingers are disposed within the collet sheath, the fingers are configured to fit within the groove provided on the occluder.

In one aspect, a delivery system for the device is provided within (and includes) a delivery sheath. In certain embodiments, the delivery system includes a first securement system for securing a first end of the occluder and a second securement system for securing a second end of the occluder. The securement systems connect the occluder to first and second catheters contained in the delivery system and enable deployment and/or retrieval of the occluder. The catheters are preferably able to move relative to each other. The securement systems enable pushing and pulling of respective ends of the occluder by manipulating the catheters to expand and contract the device. The first securement system may employ a threaded connection and the second securement system may employ a suture connection. The securement systems are detached when the device has been properly positioned.

In a further aspect of the invention, the first securement system secures a distal end of a catching system of the device and the second securement system secures a proximal end of the device. A first catheter connects to the first securement system and a second catheter connects to the second securement system. In certain embodiments, the second catheter encloses the first catheter in its central lumen. In one aspect, the device is deployed by inserting the delivery system, removing the sheath, expanding the petals of a distal portion of the device, and expanding the petals of a proximal portion of the device. The delivery system can be detached by detaching the first and second securement systems, e.g., by unscrewing the first securement system and by cutting and removing the sutures. In another aspect, the deployed device is retrieved by contracting the petals of a proximal portion of the device using the second catheter, advancing the sheath over a proximal portion of the device, contracting the petals of a distal portion of the device using the first catheter and advancing the sheath over the distal portion of the device. The occluder can then be repositioned or removed.

In another aspect, a delivery system is disclosed for delivering an occluder that closes an aperture in septal tissue. The occluder includes a first side adapted to be disposed on one side of the septal tissue and a second side adapted to be disposed on the opposite side of the septal tissue. The first and second sides are adapted to occlude the aperture upon deployment of the device at its intended delivery location. The device also employs a catch system that maintains the configuration of the device once it has been deployed. The occluder may be held in its deployment configuration by the catch element.

In one aspect, a delivery system for the device is provided within a delivery sheath. In certain embodiments, the delivery system includes a first securement system for securing a first end of the occluder and a second securement system for securing a second end of the occluder. The securement systems connect the occluder to first and second extrusions, e.g., a catheter or a wire, contained in the delivery system and enable deployment and/or recovery of the occluder. The extrusions are preferably able to move relative to each other. The securement systems enable pushing and pulling of respective ends of the occluder by manipulating the extrusions to expand and contract the device by varying its axial length. The first securement system may employ a threaded connection. The second securement system may also employ a threaded connection. The securement systems are detached when the device has been properly positioned. The securement systems can be manipulated by control systems provided in the control portion of the delivery system.

In one preferred embodiment, the invention provides a axially collapsible occluder, a means for collapsing and expanding the occluder by changing the distance between the distal and proximal ends of the occluder, and a means for keeping the axial distance between the proximal and distal ends of the occluder fixed after its deployment.

These and other aspects and embodiments of the disclosure are illustrated and described below.

BRIEF DESCRIPTION OF THE DRAWINGS

In the Drawings:

FIGS. 2A-2D are isometric views of an embodiment of an occluder for use with disclosed delivery systems and techniques;

FIGS. 4A-4D are side views of a delivery assembly for delivering an occluder to a septal defect according to an aspect of the disclosure;

FIG. 5 is a side elevational view of a delivery system attached to an occluder in deployed configuration according to an aspect of the disclosure;

FIG. 6 is an exploded cross-sectional side view of a delivery system attached to an occluder in deployed configuration according to an aspect of the disclosure;

FIG. 7 is an exploded cross-sectional side view of the control portion of a delivery system according to an aspect of the disclosure;

FIG. 8 is an enlarged cross-sectional side view of the catheter portion of a delivery system attached to an occluder according to an aspect of the disclosure;

FIG. 9 is a cross-sectional side view of the catheter portion of the delivery system attached to a collapsed occluder according to an aspect of the disclosure;

FIG. 10 is a cross-sectional side view of one step in a deployment sequence according to an aspect of the disclosure;

FIG. 22 is an axial cross-sectional drawing of an occluder, in a delivery configuration, according to an embodiment of the disclosure;

FIG. 23 is a detail view of the delivery wire according to an aspect of one embodiment of the disclosure;

FIG. 24 is a configuration for a first securement system according to an embodiment of the disclosure;

DETAILED DESCRIPTION

The present disclosure provides devices, delivery/retrieval systems and techniques for delivering such devices intended to occlude an aperture within body tissue. In particular and as described in detail below, the described occluder may be used for closing an ASD or PFO in the atrial septum of a heart. Although the embodiments are described with reference to an ASD or PFO, one skilled in the art will recognize that the device and methods of the present invention may be used to treat other anatomical conditions. As such, the invention should not be considered limited in applicability to any particular anatomical condition. In addition, the systems and methods for delivery and retrieval, and for catching a device in a deployed state, which are aspects of the present invention may also be used in connection with other types of devices besides an occluder, in particular, devices having tubular profiles.

Figure 1:
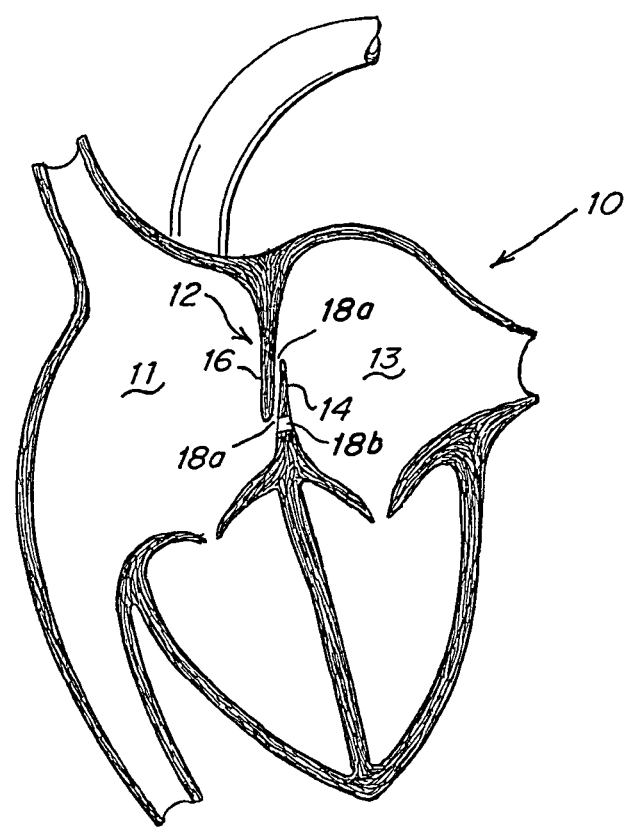
FIG. 1 is a schematic representation of a human heart including various septal defects.

FIG. 1 illustrates a human heart 10, having a right atrium 11 and a left atrium 13 and including various anatomical apertures 18a and 18b. The atrial septum 12 includes septum primum 14 and septum secundum 16. The anatomy of the septum 12 varies widely within the population. In some people, septum primum 14 extends to and overlaps with septum secundum 16. The septum primum 14 may be quite thin. When the anatomical apertures 18a is present, blood could travel through the anatomical aperture 18a between septum primum 14 and septum secundum 16 (referred to as "the PFO tunnel"). Additionally or alternatively, the presence of an ASD could permit blood to travel through an aperture in the septal tissue, such as through the anatomical aperture 18b.

In this application, "distal" refers to the direction away from a catheter insertion location and "proximal" refers to the direction nearer the insertion location. Additionally, the term "delivery configuration" refers to the configuration of a device, such as an occluder, when it has a reduced profile in a delivery catheter. The term "deployed configuration" refers to the configuration of the device, such as an occluder, when it has deployed from the catheter, such as at the desired implantation location.

FIGS. 2A-D illustrates an exemplary occluder with which systems and techniques disclosed herein may be used. An occluder 70, for example, can be formed by cutting a series of slits on tube 25. As shown in FIGS. 2A-2D, distal petals 32 are produced by cutting slits 31 in the upper portion of tube 25 according to the cutting pattern shown in FIG. 2A. As shown in FIG. 2B, the distal portion of the tube 25 is cut in half to form half sections 91a and 91b. The half sections 91a and 91b are further cut to a proximal distance from distal tip 39 into quarter sections 92a, 93a, 92b, and 93b. The cuts are discontinued and quarter sections 92a and 92b form half section 94a at distal tip 39, and quarter sections 93a and 93b form half section 94b at distal tip 39. Upon application of force $F_d$ to distal tip 39, struts defined by slits 31 bow and twist outward to form distal petals 32 in distal side 30, as shown in FIGS. 2C-2D. The movement of the struts during deployment is such that the struts rotate in an orthogonal plane relative to the axis of the device. Central tube 22 may be constrained during the application of force $F_d$, or any combination of forces sufficient to reduce the axial length of the tube 25 may be applied. One end of each of distal petals 32 originates from central tube 22, while the other end originates from distal tip 39 (FIGS. 2B-2C). Proximal petals 42 may be formed in proximal side 40, as shown in FIGS. 2B-2D, making slits 41 between central tube 22 and proximal end 44, using the same cutting pattern described above.

The tube(s) 25 forming occluder 70 may be formed from a biocompatible metal or polymer. In at least some embodiments, the occluder 70 is formed of a bioabsorbable polymer, or a shape memory polymer. Shape memory polymers can be advantageous so that the structure of the device assists in pressing the PFO tunnel closed. In other embodiments, the occluder 70 is formed of a biocompatible metal, such as a shape memory alloy (e.g., nitinol). The thermal shape memory and/or superelastic properties of shape memory polymers and alloys permit the occluder 70 to resume and maintain its intended shape in vivo despite being distorted during the delivery process. Alternatively, or additionally, the occluder 70 may be formed of a bioabsorbable metal, such as iron, magnesium, or combinations of these and similar materials. Exemplary bioabsorbable polymers include polyhydroxyalkanoate compositions, for example poly-4-hydroxybutyrate (P4HB) compositions, disclosed in U.S. Pat. No. 6,610,764, entitled Polyhydroxyalkanoate Compositions Having Controlled Degradation Rate and U.S. Pat. No. 6,548,569, entitled Medical Devices and Applications of Polyhydroxyalkanoate Polymers, both of which are incorporated by reference in their entirety.

The cross-sectional shape of tube 25 may be circular or polygonal, for example square, or hexagonal. The slits 31 and 41 may be disposed on the face of the polygon (i.e., the flat part) or on the intersection of the faces.

The tube can be injection molded, extruded, or constructed of a sheet of material and rolled into a tube. The sheet of material could be a single ply sheet or multiple ply. The slits that form the struts could be cut or stamped into the sheet prior to rolling the sheet into a tube to connect the ends to form an enclosed cross section. Various geometrical cross sections are possible including circular, square, hexagonal and octagonal and the joint could be at the vertex or along the flat of a wall if the cross section is of a particular geometery. Various attachment techniques could be used to join the ends of the sheet to form a tube, including welding, heat adhesives, non-heat adhesives and other joining techniques suitable for in-vivo application.

The petal configuration is the deployed configuration. The occluder 70 can be secured in the petal configuration by a catch system that holds the ends of the tube 25 together, certain embodiments of which are described below. Use of the terms distal and proximal sides or portions 30 and 40, respectively, include the petals that are formed on the distal and proximal sides.

The embodiment described in conjunction with FIGS. 2A-2D has similarities to the device disclosed in U.S. patent application Ser. No. 10/890,784, entitled Tubular Patent Foramen Ovale (PFO) Closure Device with Locking Mechanism, filed on Jul. 14, 2004; U.S. Patent Application No. 60/549,741, entitled Delivery/Recovery System for Clover Leaf Septal Occluder, filed on Mar. 3, 2004; U.S. Patent Application No. 60/612,857, entitled Delivery/Recovery Systems for PFO Occluder with Catch System, filed Sep. 24, 2004; U.S. Patent Application No. 60/663,289, filed Mar. 18, 2005, entitled Delivery/Recovery System for PFO Occluder with Catch System; U.S. Patent Application No. 60/662,990, filed Mar. 18, 2004, entitled Suture Delivery/Recovery System for PFO Occluder with Catch System; all of which have the same assignee as the present application, and are incorporated by reference in their entirety. These incorporated documents describe how a device can be formed by making cuts or slits in a tube and compressing the ends, and how to deliver such a device.

The transformable design of occluder 70 enables occluder 70 to be delivered in a low profile, tubular form and to be converted readily, i.e., by reducing the axial length, in place to the high-profile deployed configuration. Moreover, the conversion can readily be effected by forcing distal end 39 and proximal end 44 together. For example, distal side 30 and proximal side 40 of occluder 70 may be deployed in separate steps, or both distal side 30 and proximal side 40 of occluder 70 may be exposed (e.g., out of the delivery catheter) prior to engaging the catch system and deployed together as the catch element is engaged. Use of the terms distal and proximal side 30 and 40, respectively, include the loops or other geometries and configurations that are formed on the distal and proximal sides, respectively.

Occluder 70 may be prepared for delivery to an aperture 18 in any one of several ways. Slits 31 and 41 may be cut such that tube 25 bends into its intended configuration following deployment in vivo. Specifically, slits 31 and 41 may be cut to produce struts 32 and 42 of a thickness that facilitates the bending and formation of loops 32 and 42 upon the application of forces $F_d$ and/or $F_p$ during deployment. See FIGS. 2B and 2C. Alternatively and/or additionally, a tube 25 formed of a shape memory material may be preformed into its intended configuration ex vivo so that it will recover its preformed shape once deployed in vivo. According to at least some embodiments, this preforming technique produces more reliable deployment and bending of occluder 70 in vivo. An intermediate approach may also be used: tube 25 may be only slightly preformed ex vivo such that it is predisposed to bend into its intended shape in vivo upon application of forces $F_d$ and $F_p$.

Figure 2E:
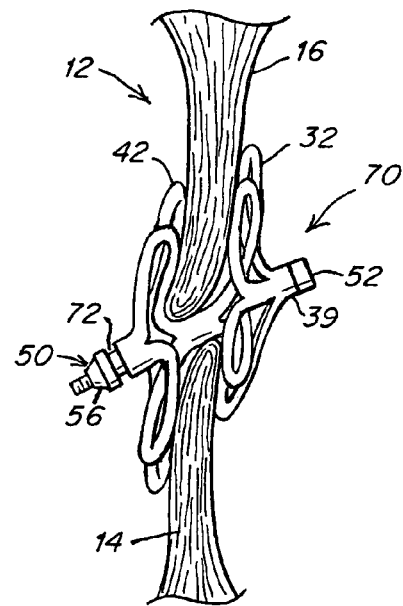
FIG. 2E illustrates a deployed occluder according to an aspect of the disclosure.

FIG. 2E shows a deployed occluder 70 in a human heart with a catch element 50 engaged. The term "catch system" describes the portion/aspect of the device that secures the device in the deployed configuration, it may be a single piece or a group of connected or assembled pieces. The catch element is the portion of the catch system that engages with the occluder to hold the occluder in the deployed configuration and is described in more detail below. The configuration illustrated is a simplified schematic view of the occluder 70 illustrated in FIGS. 2A-2D. This particular type of occluder 70 and catch element 50 are described for purposes of illustration and explanation; of course, other types of occluders (with different types of catch elements or systems) can be deployed using the deployment systems described herein. The catch element 50, as illustrated, is disposed in an axially central location in the occluder 70 and is schematically illustrated as a separate piece than the occluder 70. In a preferred embodiment, the catch element may be fixed to one end of the tube 25 that forms occluder 70. For example, a flange 52 may be fixed to the distal tip 39 of the tube 25 that forms the distal and proximal petals 32 and 42.

In general, references to "occluder 70" herein may be inclusive of catch element 50, depending on the context, for example, unless separately listed or otherwise stated. One end of tube 25 is able to move with respect to the catch element 50 (and especially the catch system) so that the distal and proximal petals 32 and 42 can move from the delivery configuration to the deployed configuration. The inside surface of the tube 25 is able to slide over the catch element 50 so that, when the proximal end 44 of the occluder 70 rests against the surface of the proximal flange 56, the occluder 70 is secured in its deployed configuration. The catch element 50 is included in the catch system that includes a portion for connection to the delivery/recovery system, including, for example, a threaded section illustrated in FIG. 2E. The threaded section is an adaptation designed to fit with the desired type of securement system according to a preferred embodiment discussed herein and is not necessarily an inherent feature of the catch element 50. Occluder 70 also includes an additional feature, such as threads or a groove 72 (as illustrated) to provide another connection between the occluder and the delivery/recovery system.

Figure 3A:
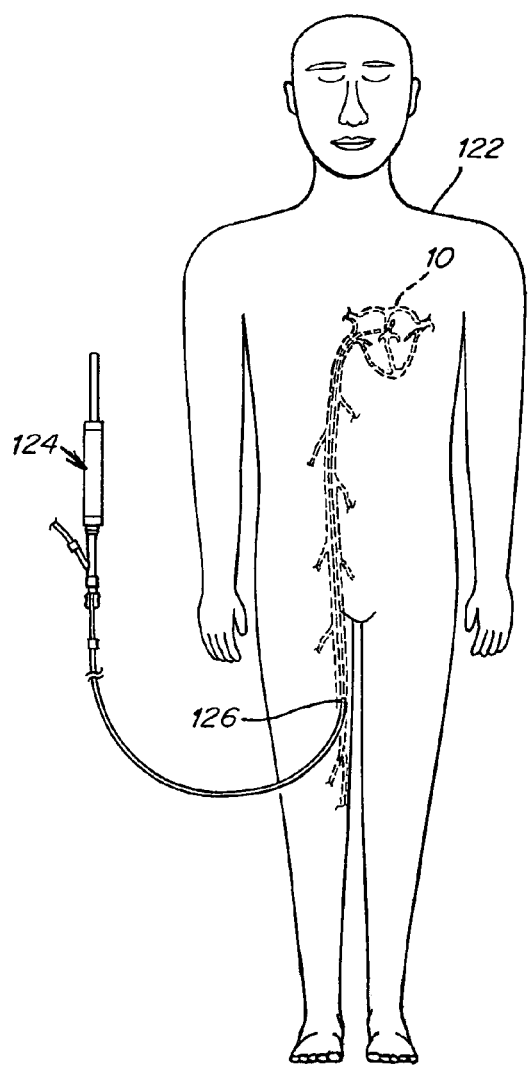
FIG. 3A illustrates insertion of an occluder in a human subject using a delivery system in accordance with an aspect of the disclosure.
Figure 3B:
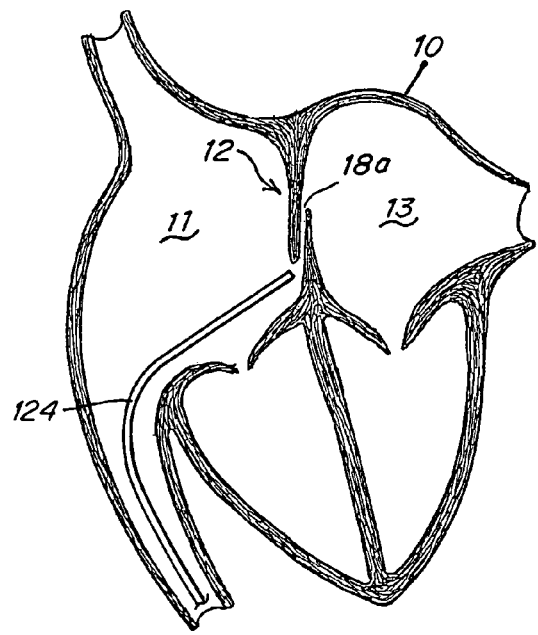
FIG. 3B illustrates introduction of the occluder in a human heart using a delivery system in accordance with an aspect of the disclosure.

FIG. 3A illustrates the insertion of an occluder in a human subject 122 using a delivery assembly 124 in accordance with an aspect of the disclosure. A portion of delivery assembly 124, including an occluder and a delivery mechanism for the occluder, which can be externally manipulated by a clinician, is inserted into the subject through an incision point 126. The distal end of the delivery assembly is advanced toward and into the heart 10 until the distal end is in proximity to the defect to be closed, as seen in FIG. 3B.

FIG. 4A illustrates the occluder 70 in the distal end of the delivery assembly 124, which includes a delivery system 140. A delivery system generally includes a delivery catheter, a delivery wire and a delivery sheath. Because the occluder 70 is delivered percutaneously, the device is secured to the delivery system 140 so that the occluder 70 can be placed accurately at the desired delivery location. Securement systems are provided that attach the occluder to the delivery components. The securement systems are configured to provide accurate delivery of the occluder to the desired delivery location and allow for a controlled deployment so that the position of the device as it is being deployed can be monitored. Also, a device deployed according to this system is able to be retrieved and repositioned until the final stage of the deployment process. In some circumstances, after the final stage of the deployment process, the device can be retrieved. The manner in which the occluder is secured to the delivery system 140 and the process for deployment and/or retrieval of the occluder 70 are described in detail below.

As illustrated in FIG. 4A, the delivery system 140 includes a delivery sheath 144 and a delivery catheter 148. A delivery string or wire 150 extends the length of the delivery assembly to the distal end of the occluder 70. The delivery system 140 constrains the occluder 70 in its elongated delivery configuration. As shown in FIG. 4B, a delivery sheath 144 containing the occluder 70 is first inserted into the right atrium 11 of the patient's heart.

Figure 4C:
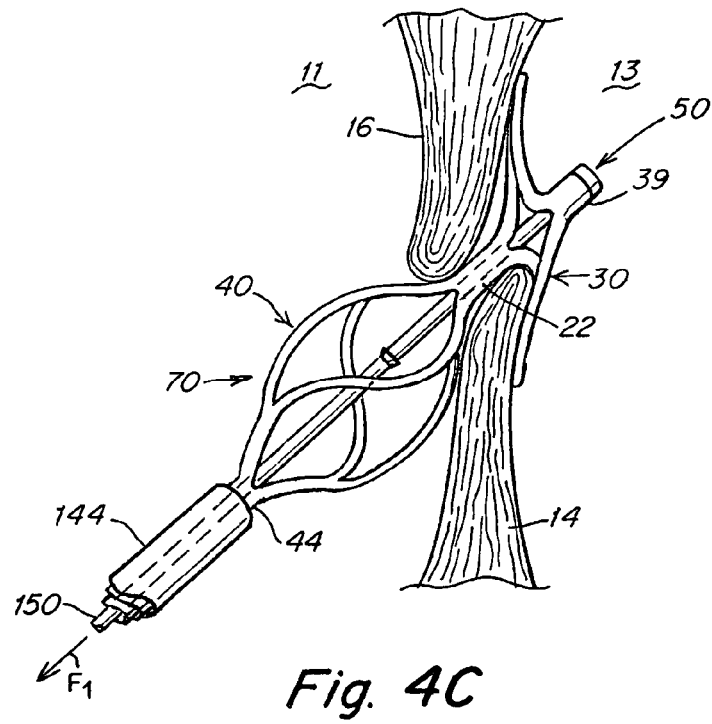

The delivery system, including the delivery sheath 144, may next be inserted through aperture 18 located in the septal tissue 12 (which, in this example, is a PFO tunnel) and into the left atrium 13. Distal side 30 of occluder 70 is then exposed into the left atrium 13 by withdrawing the delivery sheath 144 then pulling force $F_1$ is applied to delivery string or wire 150 such that, for example, a catch element 50 passes through the central tube 22, thereby securing distal side 30 into its deployed state. Delivery sheath 144 is withdrawn further through the aperture 18 and into the right atrium 11, such that central tube 22 is positioned through the aperture 18. As shown in FIG. 4C, proximal side 40 of occluder 70 is then exposed into the right atrium 11, and a relative force between the proximal end 44 of the occluder 70 and the delivery string or wire 150 is applied such that a catch element 50 passes through the proximal end 44 of the occluder 70, thereby securing the proximal side 40 of the occluder into its deployed state. Of course, the occluder 70 should remain in position during deployment of each side of the occluder 70 and pulling forces on the septum tissue should be avoided.

Figure 4D:
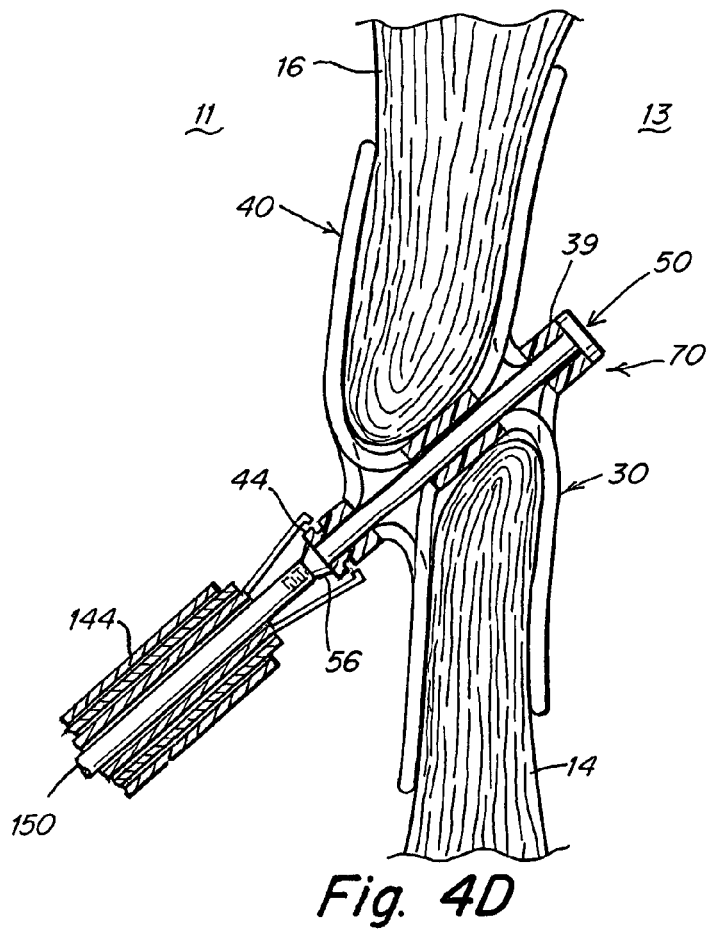

As shown in FIG. 4D, when properly deployed, occluder 70 is disposed through the aperture 18 with a portion of the device on the proximal side and another portion of the device on the distal side. The distal side 30 and proximal side 40 exert a compressive force against septum primum 14 and septum secundum 16 in the left 13 and right 11 atria, respectively, to close the aperture 18, e.g. the PFO. When the occluder 70 is properly located, the securement systems are detached releasing the occluder from the delivery system. This delivery system is then removed from the heart. In the event occluder 70 is not properly deployed after performing the delivery sequence, the occluder 70 may be recovered by reversing the steps of the delivery sequence.

As mentioned above, during the deployment of the occluder 70 in the delivery system 140 described in connection with FIGS. 4A-4D, the occluder 70 is secured to the delivery system 140 at two locations on the occluder 70 so that the occluder 70 can be formed (i.e., compressed) into its deployed configuration. In a preferred form, there are two securements to the delivery assembly 140. A first securement is toward the distal end of the occluder 70 whereby the occluder 70 is held by the delivery string or wire 150. The second securement is at the proximal end 44 of the occlude 70 whereby the occluder 70 is held by the delivery catheter 148. The first and second securements allow the proximal and distal ends of the occluder 70 to be forced together so that the occluder 70 can move from the delivery configuration to the deployed configuration. They also allow the occluder 70 to be forced back into its low profile delivery configuration for redeployment or retrieval. Even if the occluder 70 were constructed from shape memory material (e.g., Nitinol), the occluder 70 would preferably be secured to the delivery assembly 140 by first and second securements.

Both securement systems are able to move relative to one another during the delivery process and as a result, both securement systems cause the occluder 70 to move into the deployed configuration. In the process of delivering the occluder 70, the second securement system is typically released and the first securement system is held while the position of the occluder 70 is evaluated by, for example, fluoroscopy, and if the position of the occluder 70 is appropriate, the first securement system is released.

FIG. 5 shows delivery assembly 200, which includes a delivery system 220 with an occluder 224 to be delivered. The attached occluder 224 is shown in a deployed configuration for convenience only. Prior to deployment, the occluder 224 would normally be in a low-profile configuration, contained within a delivery sheath 242. FIG. 6 shows delivery assembly 200 in an exploded cross-sectional side view. For convenience, the illustrations have been divided into two parts comprising a control portion 230 of the delivery system 220, and a catheter portion 250 of the delivery system 220 with the attached occluder 224, with the connection indicated by broken line L1. The control portion 230 extends from a delivery wire control rod 232 to a delivery sheath control 240. The catheter portion 250 extends from the delivery sheath control 240 to the end of the delivery system 220 where the occluder 224 is attached. The control portion 230 remains external to the patient and incorporates the features provided for operation of the catheter portion 250 of the delivery system 220. FIG. 7 shows an enlarged cross-sectional side view of the control portion 230. FIG. 8 shows an enlarged cross-sectional side view of the catheter portion 250 and the occluder 224. The basic components of the delivery system 220 are described below by reference to FIGS. 5-8 collectively.

For convenience in describing the function of the controls, the catheter portion 250 is discussed first. Now, referring to FIG. 6, in the catheter portion 250, a delivery sheath 242 encloses the components that are used to deliver occluder 224. A delivery catheter 244 contains an inner delivery wire 246. Both of the delivery catheter 244 and delivery wire 246 connect to the occluder 224 during delivery. Although it may be considered advantageous to eliminate the central lumen in certain embodiments, in other embodiments the delivery wire 246 could also be tubular. The delivery wire 246 should have sufficient tensile and compressive stiffness to withstand the steps required for the deployment and retrieval sequence. In this embodiment, the delivery wire 246 has a stiffer proximal portion and a more flexible distal portion. The delivery catheter 244 also has a stiffer proximal portion and a more flexible distal portion. The combination of stiffness and flexibility facilitates delivery and positioning of the occluder 224. Both the delivery catheter 244 and the delivery wire 246 may be made of two lengths of two different materials joined together in order to provide the requisite degree of stiffness in each portion of the element. Alternatively, the variation of stiffness can be the result of annealing, or some other material treatment process. The more flexible distal portion prevents undue distortion of the septal tissue during the delivery sequence. The delivery wire is further described infra.

Still referring to FIG. 6, the control portion of the delivery system 230 includes respective controls for the delivery sheath 242, the delivery catheter 244 and the delivery wire 246. The delivery wire 246 can be advanced and retracted linearly, in the direction indicated by arrow C', and rotated with respect to the linear axis of the delivery system 220, in the direction indicated by arrow D'. The delivery wire control rod 232 is a rod-like element that provides both linear and rotational control for the delivery wire 246. The delivery wire control rod 232 slides linearly in the direction indicated by arrow C and rotates, with respect to the linear axis of the delivery system 220, in the direction indicated by arrow D to provide the corresponding motion in the delivery wire 246. The delivery catheter 244 can be advanced and retracted linearly, in the direction indicated by arrow A', and rotated, with respect to the linear axis of the delivery system 220, in the direction indicated by arrow B'. A delivery catheter control 234 is a tubular element that provides linear control for the delivery catheter 244, by sliding linearly in the direction indicated by arrow A. A delivery catheter rotational control 238 provides rotational control of the delivery catheter 244, by rotating, with respect to the linear axis of the delivery system 220, in the direction indicated by arrow B. The delivery wire control rod 232 connects to the delivery wire 246 inside the delivery catheter control 234. A perfusion port 236 is provided to permit introduction of fluids into the delivery sheath 242. The delivery sheath 242 can also be rotated, with respect to the linear axis of the delivery system 220, in the direction indicated by arrow F' and extended and retracted linearly along the direction indicated by arrow E'. A delivery sheath control 240 provides linear and rotational control of the delivery sheath 242. The delivery sheath control 240 can be rotated, with respect to the linear axis of the delivery system 220, in the direction indicated by arrow F and slided linearly in the direction indicated by arrow E to induce the corresponding motion in the delivery sheath 242. Thus, all three of the delivery sheath 242, delivery catheter 244 and delivery wire 246 can be independently extended and retracted along and rotated around the longitudinal axis of the delivery system 220 relative to each other using the appropriate controls. The controls are preferably designed to ergonomic specifications. Coordinated operation of the delivery sheath 242, delivery catheter 244 and delivery wire 246 allows for delivery (or retrieval) of the occlude 224. Although in the illustrated embodiment, each element of the catheter portion 250 can be manipulated individually and directly by the user of the delivery system 220, in alternate embodiments, the required operations could be partially or completely automated or synchronized.

Since the occluder 224 is delivered percutaneously, the delivery system 220 must be able to be secured so that the occluder 224 can be placed accurately at the desired delivery location and transformed into its deployed configuration. Securement systems are provided that attach the delivery components to the occluder 224. The securement systems are typically released serially after proper placement of the occluder 224 is confirmed. The securement systems are configured to provide accurate delivery of the occluder 224 to the desired delivery location and allow for a controlled deployment. Also, a device deployed according to this mechanism is able to be retrieved and repositioned until the final stage of the deployment process. It is also possible to retrieve the device once it has been fully released.

Referring to FIG. 8, the delivery catheter 244 and delivery wire 246 both contain features of securement systems on their distal ends for connecting to the occluder 224 and a catch system 180. The delivery wire 246 terminates in a threaded portion 258 having a funnel-like profile. The threaded portion 258 screws onto a mated threaded portion 182 provided on the proximal flange 184 of the catch element 188 for the occluder 224. These two threaded portions cooperatively form the first securement system. The delivery catheter 244 terminates in a threaded portion 256 having a funnel-like profile. The threaded portion 256 screws onto a mated threaded portion 226 provided on the frame of occluder 224. These two threaded portions cooperatively form the second securement system. The first securement system in effect secures the distal end of the occluder to the delivery system 220. The second securement system secures the proximal end 44 of the occluder 224 to the delivery system 220. The two-securement systems cooperatively allow the ends of the occluder 224 to be forced together or apart for deployment or retrieval. The funnel-like profile is useful for locating the corresponding threaded portion of the occluder 224 or the catch element 188 for attachment. The funnel provides a channeling or guiding function. The funnel also helps the delivery system 220 attach to the occluder 224 at extreme angles. The specific geometry of the funnel tips can be modified to achieve better alignment with the device. Application of torque in the appropriate direction engages or disengages each securement system by screwing together or unscrewing the respective elements from each other. The terms "distal" and "proximal" generally refer to the disposition of the securement locations while the occluder 224 is in the delivery configuration in a delivery sheath, but the orientation of the securement systems may change during or after the delivery process.

Still referring to FIG. 8, in a presently preferred embodiment, the threaded portions 256 and 258 are both female threaded, while the corresponding threaded portion 182 of the proximal flange 184 and threaded portion 226 are male threaded. This configuration has several advantages. First, a male thread in the occluder eliminates a cavity in the occluder 224 in which blood can stagnate and promote clotting. Second, the profile of the occluder 224 is reduced by using the male thread. Finally, the female connectors on the delivery system 220 can be provided with the funnel-like guides described above. In alternate embodiments, the male threads may be disposed on threaded portions 256 and 258. Also, threaded portions 256 and 258 need not have the same type of threads.

Figure 11:
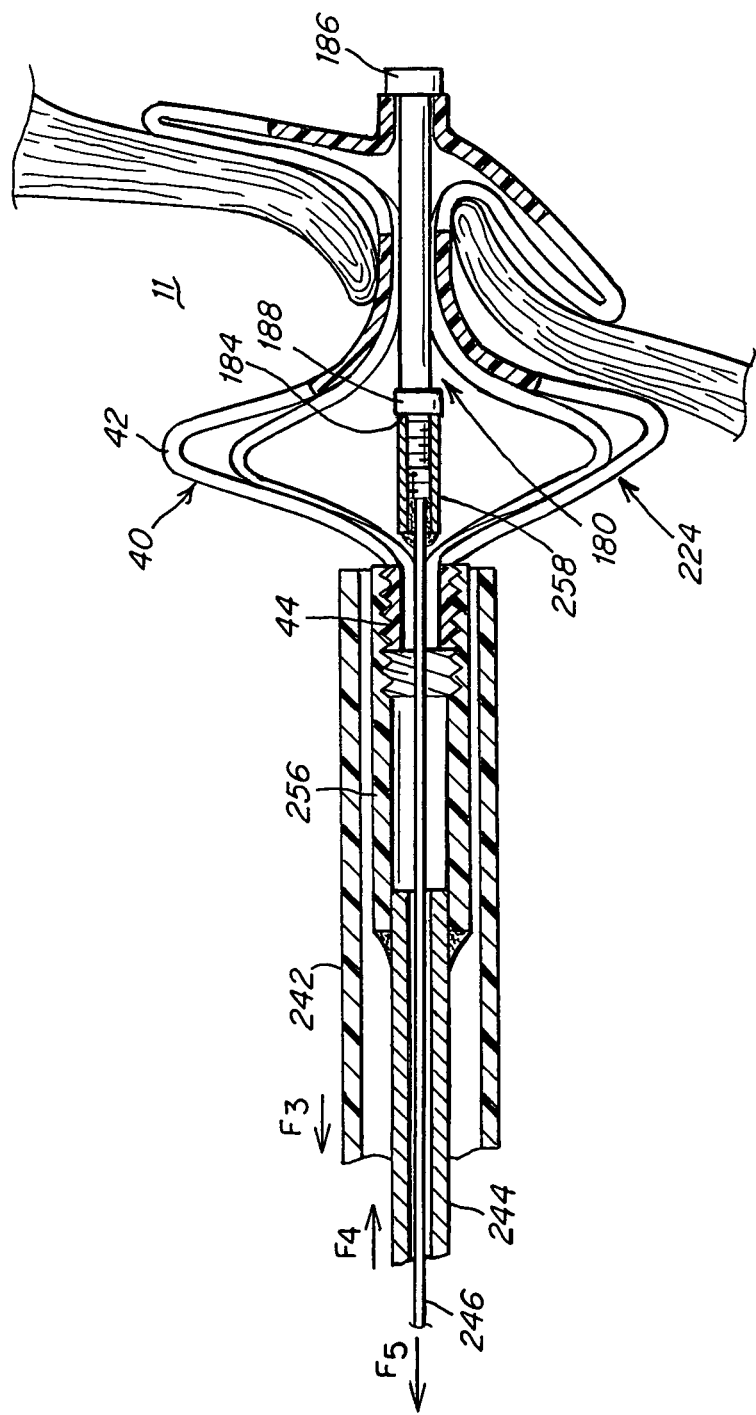
FIG. 11 is a cross-sectional side view of one step in a deployment sequence according to an aspect of the disclosure.

Deployment of the occluder to a desired site is typically a multi-step operation. In FIGS. 5 and 6, the occluder 224 is shown outside the delivery catheter for purposes of illustration. As shown in FIG. 9, the delivery sheath 242 contains occluder 224 in its elongated, delivery form, with the catch element 188 disengaged. As discussed above with reference to FIGS. 3A and 3B, the distal end of the delivery sheath 242 with the enclosed occluder 224 is first inserted into the right atrium 11 of the patient's heart. The distal end of the delivery sheath 242 with the enclosed occluder 224 may next be inserted through the anatomical aperture 18a located in the septal tissue 12, and into the left atrium 13. The distal side 30 of occluder 224 is then deployed into the left atrium 13. The deployment process is described further below. As shown in FIG. 10, the delivery sheath 242 is withdrawn through the anatomical aperture 18a into the right atrium 11, such that central tube 22 of the occluder 224 is positioned through the anatomical aperture 18a. As shown in FIG. 11, the proximal side 40 of the occluder 224 is then deployed into the right atrium 11. When properly deployed, the central tube 22 is disposed at the anatomical aperture 18a, and the distal side 30 and proximal side 40 exert a compressive force against septum primum 14 in the left atrium 13 and septum secundum 16 in the right atrium 11, respectively, to close the anatomical aperture 18a, e.g. the PFO. When the occluder 224 is properly deployed, the delivery system 220 is detached from the occluder 224, and the delivery sheath 242 with the delivery catheter 244 and delivery wire 246 are then withdrawn from the heart. In the event that the occluder 224 is not properly deployed after performing the procedure described above, the occluder 224 may be recovered by reversing the steps of the delivery sequence. These sequences are described in more detail below.

FIG. 9 illustrates the initial step for a typical delivery sequence in accordance with one aspect of the disclosure, a high level view of which is shown in FIG. 3B. The occluder 224 and catch system 180 are secured to the delivery wire 246 and to the delivery catheter 244, respectively. The female threaded portion 256 of the delivery catheter 244 is screwed onto the male threaded portion 226 of the occluder 224. The female threaded portion 258 of the delivery wire 246 is screwed onto the male threaded portion 182 of the catch element 188 of the occluder 224. The distal end of the delivery sheath 242 with the enclosed occluder 224 is inserted through the aperture to be occluded, such as the anatomical aperture 18a of FIG. 1, to approximately the midpoint of the occluder 224.

Referring now to FIG. 10, the distal side 30 of the occluder 224 is deployed on the distal side of the aperture in the left atrium 13. The distal portion 30 is deployed by first retracting the delivery sheath 242 to expose the distal portion 30 of the occluder 224. The axial length of the occluder 224 is then reduced by applying pulling force $F_1$ on delivery wire 246 with sufficient force to cause the catch element 188 to be pulled through the central tube 22 of the occluder 224 and the distal portion 30 of the occluder 224 to compress and distal petals 32 to form. Force $F_2$ is simultaneously applied to the delivery catheter 244 to hold the occluder 224 stationary. The central tube 22 of the occluder 224 catches on the catch element 188. This holds the distal petals 32 in place while the remainder of the deployment sequence is carried out.

Figure 12:
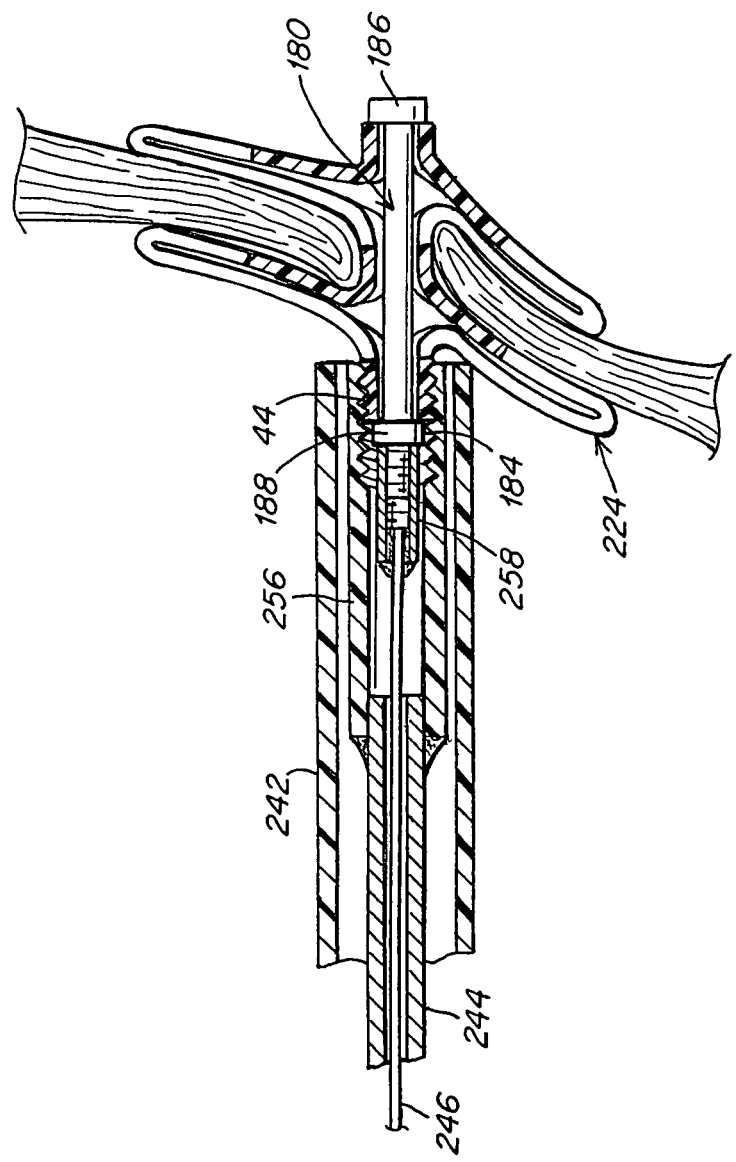
FIG. 12 is a cross-sectional side view of one step in a deployment sequence according to an aspect of the disclosure.

Referring now to FIG. 11, the proximal side 40 of the occluder 224 is deployed on the proximal side of the aperture in the right atrium 11. The proximal portion 40 is deployed by first retracting the delivery sheath 242 to expose the proximal portion 40 of the occluder 224 The proximal petals 42 are then deployed by simultaneously advancing the delivery catheter 244 by applying force $F_4$ and retracting the delivery wire 246 by applying force $F_5$ to maintain the position of the occluder 224. Eventually, the proximal end 44 of the occluder 224 is pushed over the proximal end 44 of the catch element 188 and the occluder 224 is caught on the proximal flange 184 of the catch element 188. The final configuration is illustrated in FIG. 12. The occluder 224 can now be evaluated for proper deployment at the desired location.

Figure 13:
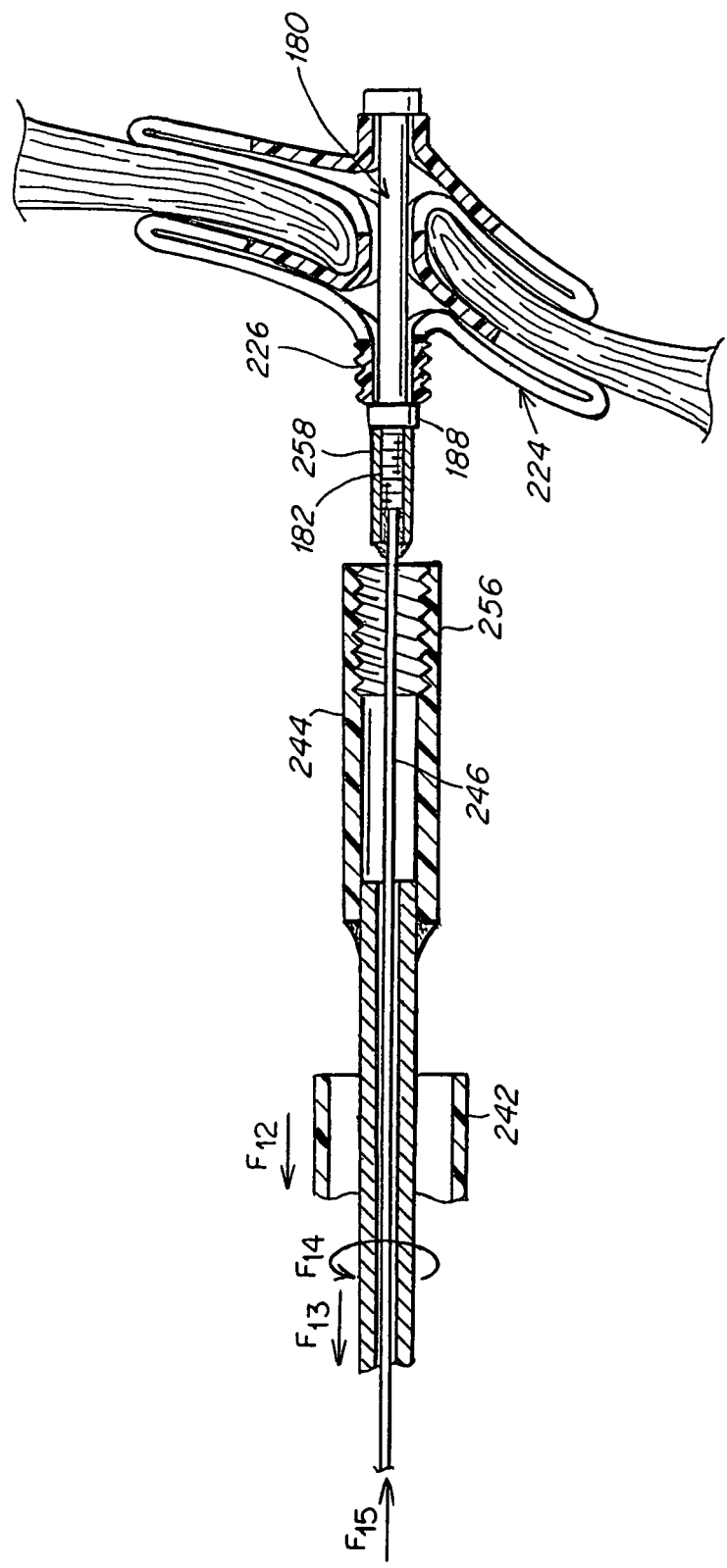
FIG. 13 is a cross-sectional side view of one step in a detachment sequence according to an aspect of the disclosure.
Figure 14:
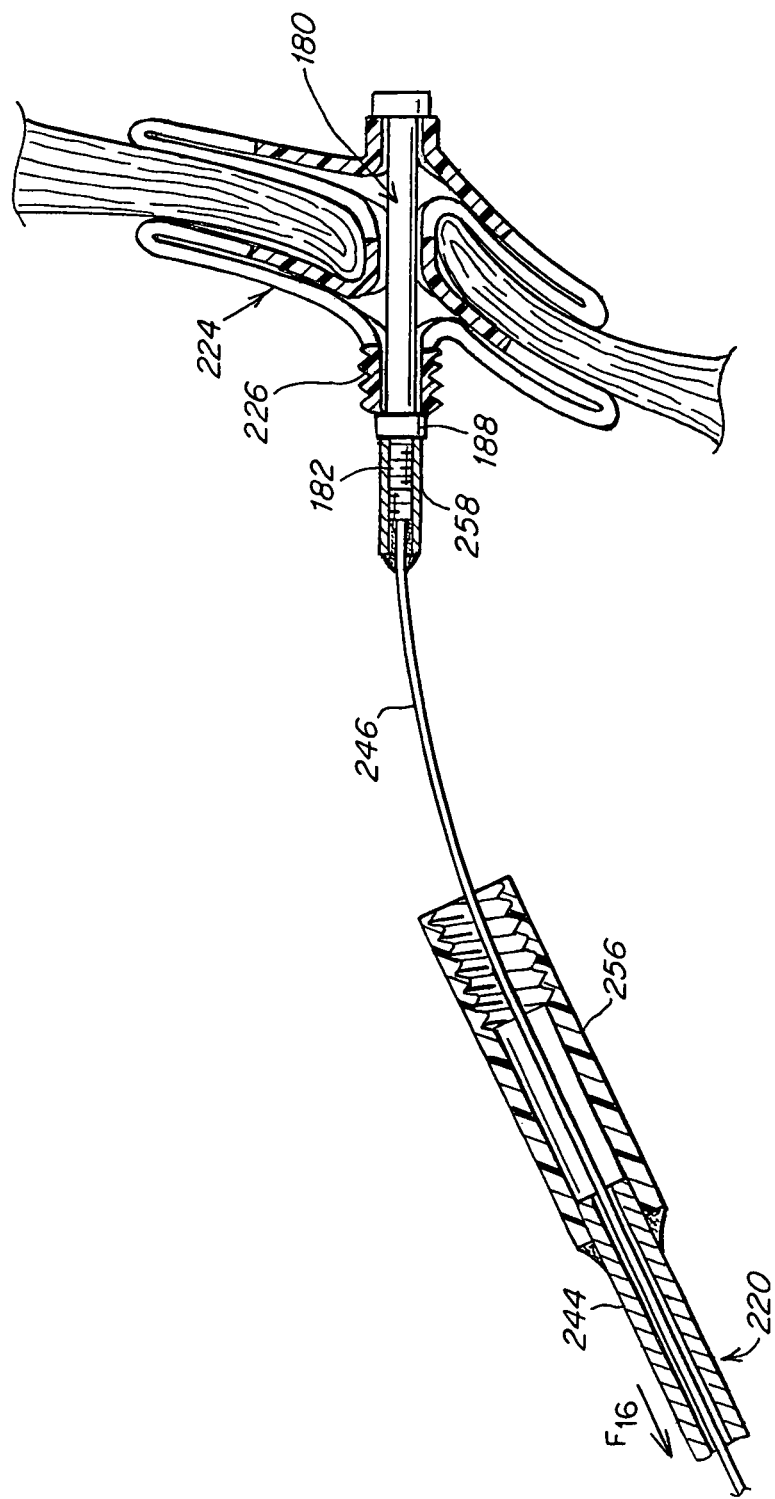
FIG. 14 is a cross-sectional side view of one step in a detachment sequence according to an aspect of the disclosure.

The occluder 224 can be evaluated for proper deployment with the delivery system 220 attached or at least partially detached. The delivery system 220 can be partially detached by releasing one of the securement systems provided by the delivery catheter 244 and the delivery wire 246. As shown in FIG. 13, according to one preferred embodiment, to evaluate the proper deployment of the occluder, if desired, the delivery sheath 242 can be further retracted and the delivery catheter 244 can be detached from the occluder 224. The delivery catheter 244 can be detached by applying torque to unscrew the delivery catheter 244 from the proximal threaded portion 226 of the occluder 224 and retracting the delivery catheter 244. The delivery wire 246 continues to secure the occluder 224, as illustrated in FIG. 14. This affords the clinician a substantially unobstructed view of the occluder delivery site in order to evaluate the placement of the occluder 224. In addition, the more flexible distal portions of the delivery catheter 244 and the delivery wire 246 allow the distal end of the delivery system 220 and the deployed occluder to be re-positioned so that the view is not obstructed. The positioning of the occluder 224 can be evaluated using fluoroscopy or other appropriate techniques. If the delivery or deployment is not satisfactory, then the delivery system 220 can be used to retrieve the occluder 224. If delivery catheter 244 has been detached, it is reattached by advancing the threaded portion 256 of the delivery catheter 244 toward the threaded portion 226 of the occluder 224 and applying torque until the delivery catheter 244 is threaded onto the occluder 224. As mentioned before, the funnel-like shape of the threaded portion 256 of the delivery catheter 244 helps to guide the reattachment of this securement system. A similar technique is used to reattach the delivery wire 246 if needed.

Figure 15:
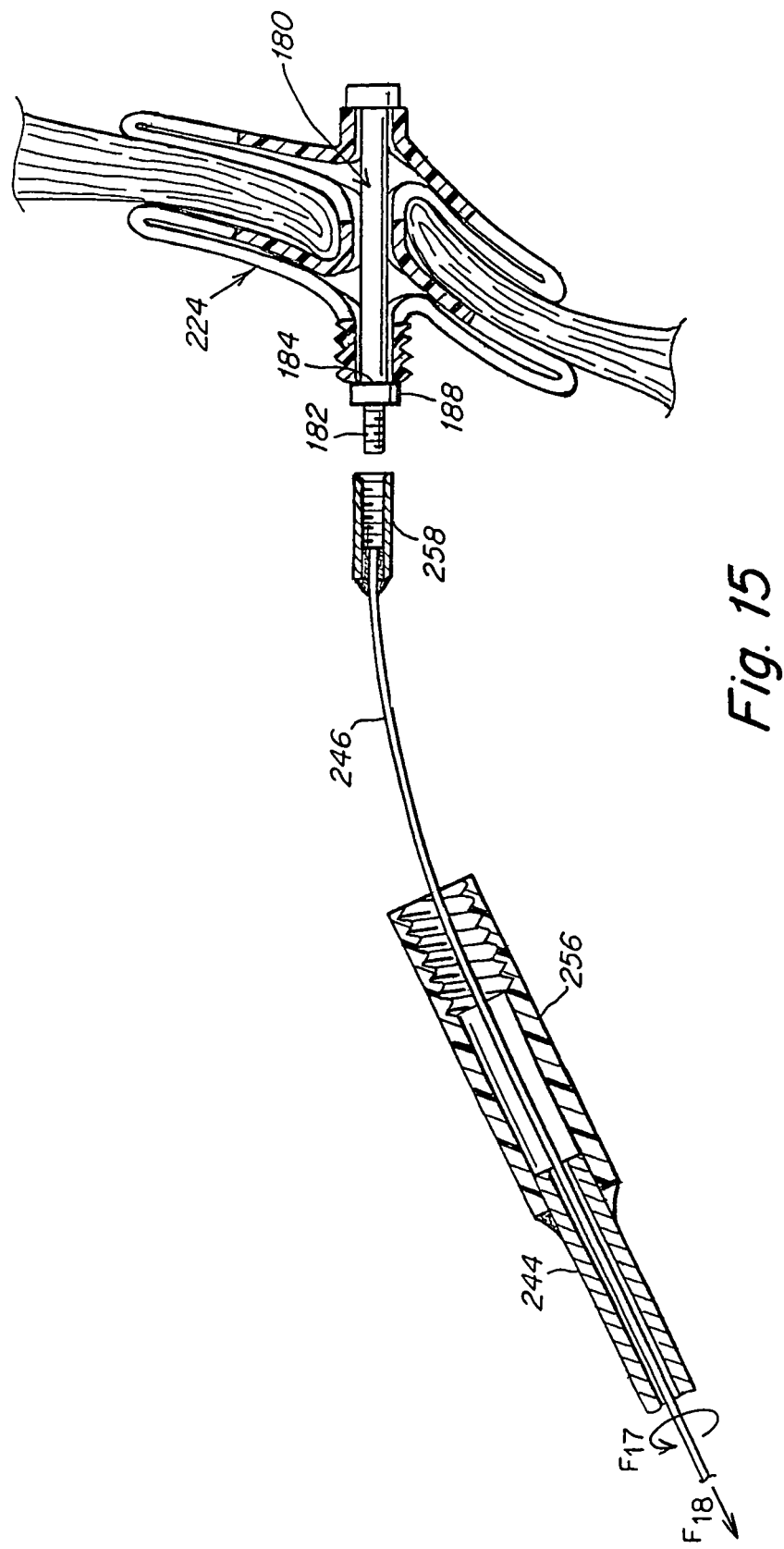
FIG. 15 is a cross-sectional side view of one step in a detachment sequence according to an aspect of the disclosure.

Once the occluder 224 is successfully deployed, the delivery system 220 can be detached in the sequence shown in FIGS. 13-15. As illustrated in FIG. 13, the delivery sheath 242 is partially retracted by applying force $F_{12}$. Also, the delivery catheter 244 is detached by applying torque $F_{14}$ to unscrew the threaded portion 256 of the delivery catheter 244 from the threaded portion 226 of the occluder 224. Force $F_{13}$ is then applied to retract the delivery catheter 244 while simultaneously advancing the delivery wire 246 by applying force $F_{15}$ to maintain the position of the occluder 224. The occluder 224 remains attached to the delivery system 220 by the second securement system provided by the delivery wire 246. As discussed above, if retrieval is desired for any reason, the occluder 224 can readily be returned to its low-profile configuration and removed at this point. As shown in FIG. 14, the delivery catheter 244 can be further retracted by applying force $F_{16}$ to provide an unobstructed view of occluder 224, again while the delivery wire 246 remains attached. As illustrated in FIG. 15, if the deployment is successful, then the delivery wire 246 can be detached by applying torque $F_{17}$ to unscrew the threaded portion 258 of the delivery wire 246 from the threaded portion 182 of the catch element 188. The torque applied to remove the delivery wire 246 and the delivery catheter 244 can be either clockwise or counterclockwise depending on the design of the device. For example, the threads associated with the first securement system can be unscrewed with a different rotational direction than the threads associated with the second securement system, or the threads associated with the first securement system can be unscrewed with the same rotational direction than the threads associated with the second securement system. The delivery wire 246 can be retracted by applying force $F_{18}$. The occluder 224 is now fully deployed.

Figure 16:
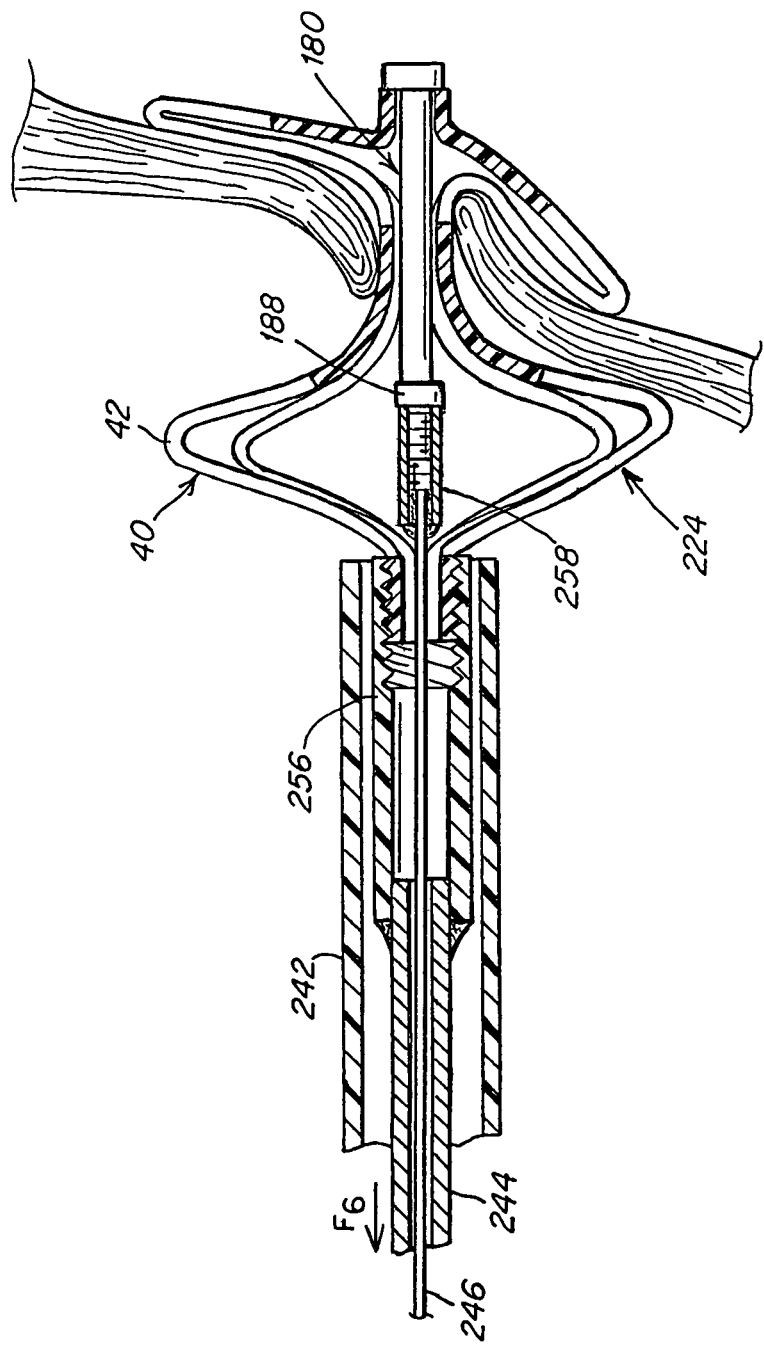
FIG. 16 is a cross-sectional side view of one step in a retrieval sequence according to an aspect of the disclosure.
Figure 17:
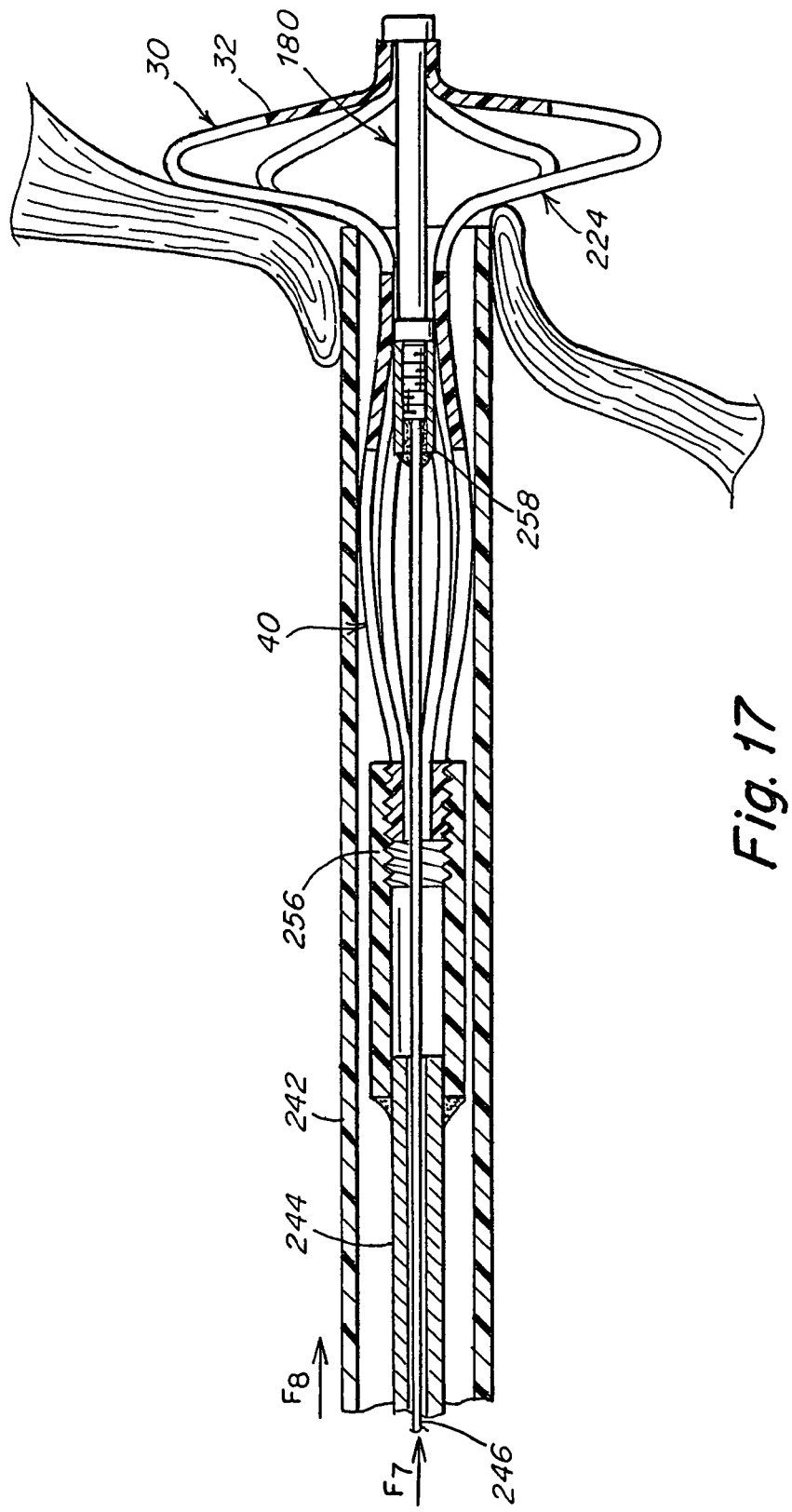
FIG. 17 is a cross-sectional side view of one step in a retrieval sequence according to an aspect of the disclosure.
Figure 18:
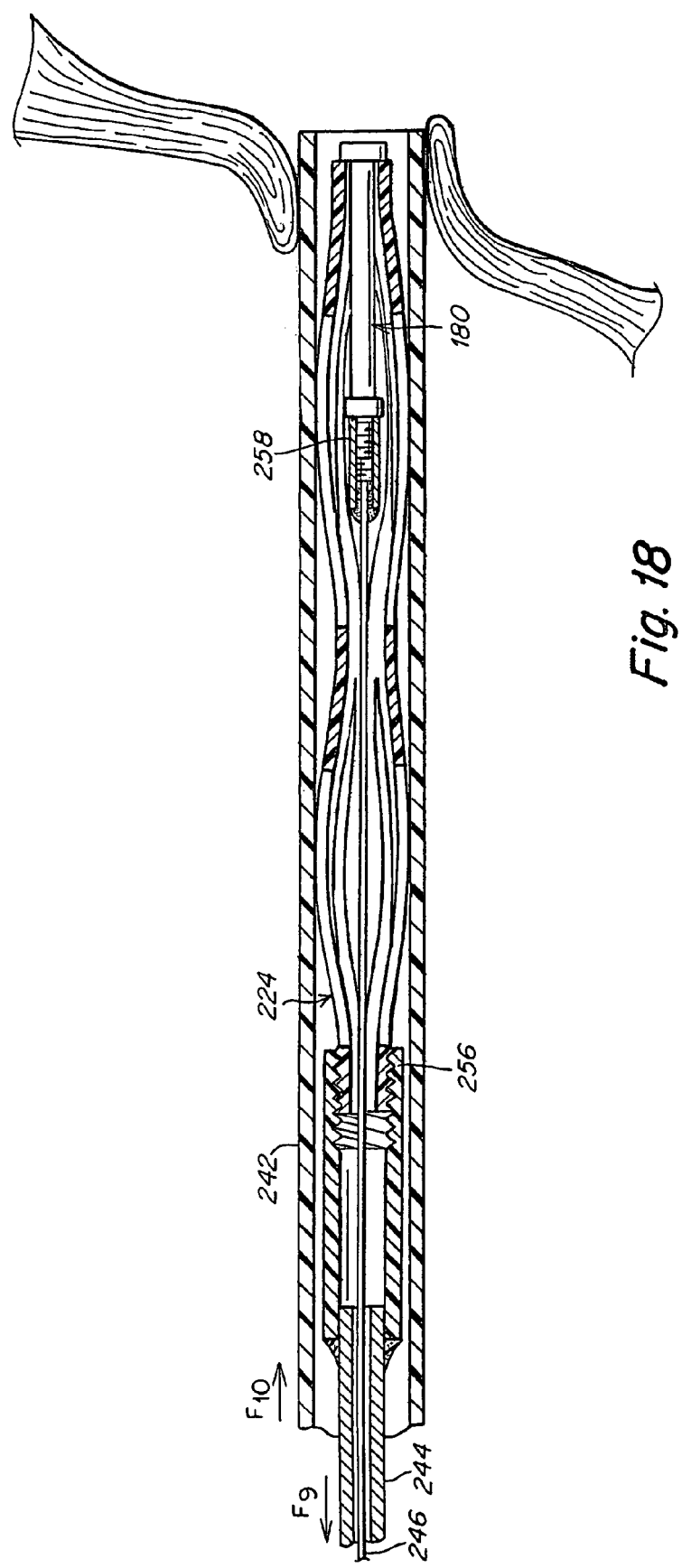
FIG. 18 is a cross-sectional side view of one step in a retrieval sequence according to an aspect of the disclosure.
Figure 19:
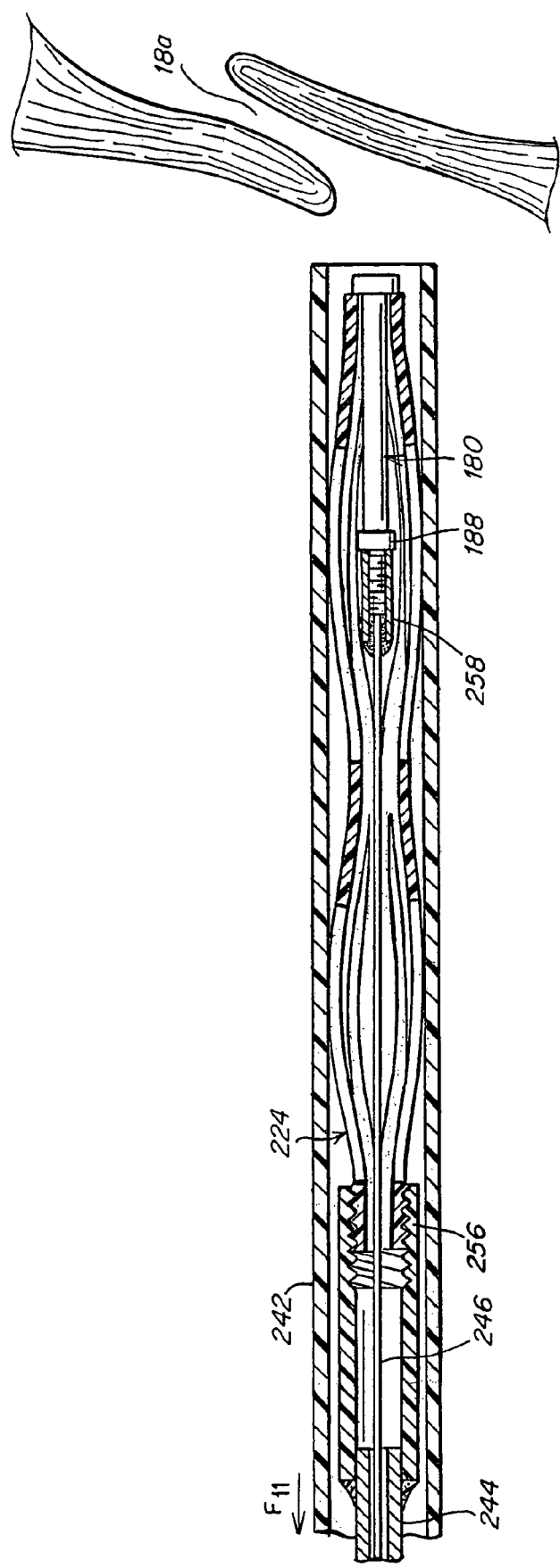
FIG. 19 is a cross-sectional side view of one step in a retrieval sequence according to an aspect of the disclosure.

Referring now to FIG. 16, if retrieval is desired, the process involves reattaching the delivery catheter 244 and delivery wire 246 as mentioned above. Then force $F_6$ is applied to the delivery catheter 244 to pull the proximal portion 40 of the occluder 224 over the proximal end of the catch element 188. As the axial length of the occluder 224 is increased, the proximal petals 42 are unformed and the proximal portion 40 of the occluder 224 returns to its tubular profile. Referring to FIG. 17, force $F_8$ is applied to the delivery sheath 242 to advance the delivery sheath 242 over the proximal portion 40 of the occluder 224 and retain the proximal portion 40 of the occluder 224 in the low-profile configuration. Also, force $F_7$ is applied to delivery wire 246 in order to release the distal portion 30 of the occluder 224 and further increase the axial length of the occluder 224. Referring now to FIG. 18, the distal portion 30 of the occluder 224 is fully extended back into it low-profile configuration and forces $F_9$ and $F_{10}$ are applied to the delivery sheath 242 and the delivery catheter 244 in order to retrieve the occluder 224 back into delivery sheath 242. Referring to FIG. 19, the delivery sheath 242 and enclosed occluder 224 are removed from the anatomical aperture 18a and can further be fully removed from the heart 10 by applying force $F_{11}$. This step can also be used as a starting point for redeployment of the occluder 224, i.e., the sequence shown beginning in FIG. 9.

Figure 20:
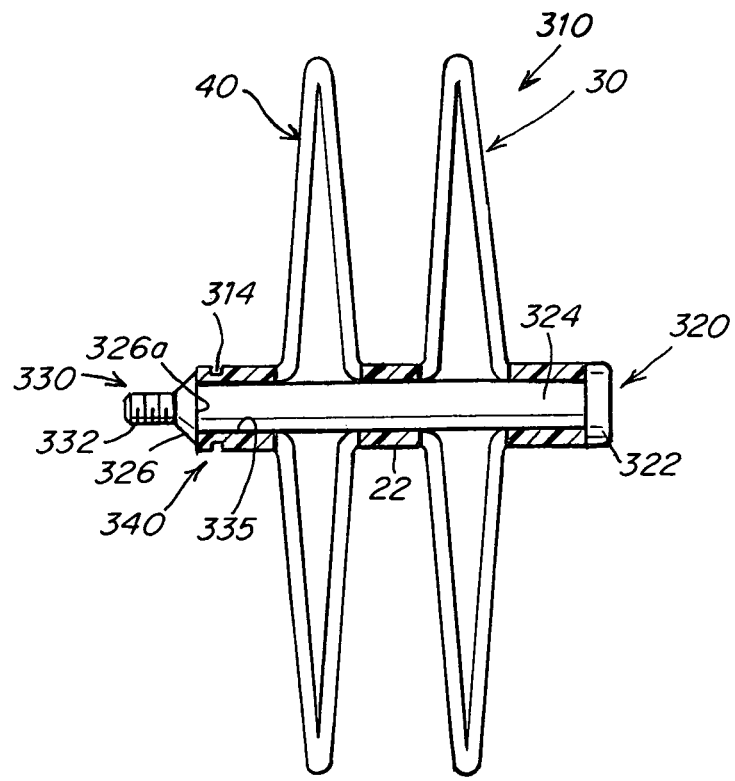
FIG. 20 illustrates a cross-sectional schematic of a deployed occluder according to an aspect of the disclosure.

The components of an alternate preferred embodiment of the invention are described in connection with FIGS. 20-24. FIG. 20 illustrates an occluder 310 with a distal side 30 and a proximal side 40 that are connected by central tube 22. The configuration illustrated is a simplified schematic view of the occluder illustrated in FIGS. 2A-2D. Of course, other types of occluders can be deployed using this delivery system. The occluder includes a catch system 320 that includes a distal flange 322, a catch body 324 and a catch element 326 in the shape of a cone. The catch system 320 is disposed in an axially central location in the occluder 310. Although schematically illustrated as a separate piece than the proximal side and distal side loops 40 and 30, respectively, of the occluder, the catch system 320 may be a single piece, or even fixed to one end of the tube that forms the proximal and distal loops by an adhesive, ultrasonic welding, or the like. For example, the flange 322 may be fixed to the end of the tube that forms the loops. The device can be formed from a single component or multiple components that are fixed together. The catch body 324 is disposed axially within the inside surface of the tube that forms the loops. The tube is able to move with respect to the catch system (and the catch body) so that the petals can move from the delivery configuration to the deployed configuration. The inside surface of the tube 335 is able to slide over the catch element 326 so that, when the proximal tip of the occluder 310 rests against the flat surface 326a of the catch element 326, the occluder 310 is secured in its deployed configuration.

Figure 21:
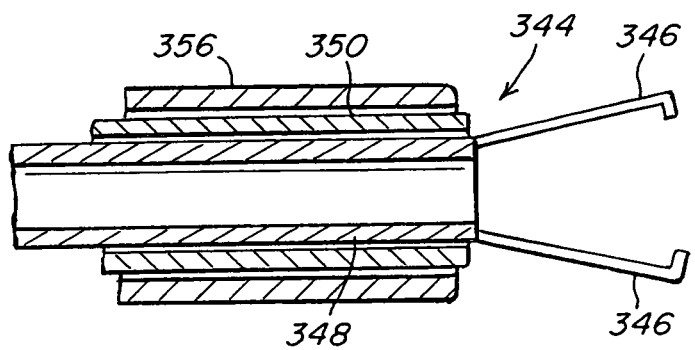
FIG. 21 illustrates a cross-sectional side view of several components of the delivery system according to one embodiment of disclosure.

As shown in FIG. 20, the first securement system 330 includes a threaded component 332, illustrated as a male thread, and corresponding threads on a corresponding female portion described below in connection with FIGS. 22 and 23. The second securement system 340 includes a groove 314 on the proximal portion 40 of the occluder 310 that cooperates with a collet system 344 described below in connection with FIGS. 21 and 22. As shown in FIG. 21, the collet system 344 also includes collet fingers 346 that are configured to have ends that fit within the groove 314 on the occluder 310. The collet system also includes a collet tube 348 onto which the collet fingers 346 are mounted and a collet sheath 350 that is movable with respect to the collet tube 348. In one embodiment, the collet fingers 346 are constructed of nitinol and have a splayed configuration when at rest as illustrated in FIG. 21. More detail regarding the construction of the construction of the collet fingers 346 is provided below. As the end of the collet sheath 350 is moved over the collet fingers 346, the collet fingers 346 are moved radially inward and when occluder 310 is being positioned in the delivery system, the collet fingers 346 are moved radially inward and engage the groove 314 on the occluder 310 (illustrated on the left side of FIG. 22). The collet sheath 350, collet tube 348 and collet fingers 346 are described in more detail below.

FIG. 22 illustrates a delivery system of a preferred embodiment of the invention. Specifically, the occluder 310 is disposed within the delivery sheath 356. Within the delivery sheath 356 are the components that are used to secure the occluder 310 during delivery and are (typically) released serially after proper placement of the occluder 310 is confirmed. The first securement system 330 and the second securement system 340 are each illustrated as securing the occluder 310 for delivery to the desired delivery location within the body. The securement systems 330 and 340 are configured to provide accurate delivery of the occluder 310 to the desired delivery location and allow for a controlled deployment so that the position of the device as it is being deployed can be monitored. Also, an occluder 310 deployed according to this system is able to be retrieved and repositioned until the final stage of the deployment process. Even after the final stage of the deployment process, the occluder 310 can be retrieved.

FIG. 22 also illustrates the second securement system 340 in an engaged configuration. Specifically, the collet fingers 346 are disposed in the collet sheath 350 so that the collet fingers 346 engage groove 314 on the occluder 310. When the collet sheath 350 is disposed in this configuration, the occluder 310 is secured by the collet fingers 346 against axial motion with respect to the collet sheath 350 and collet tube 348. Similarly, when the delivery wire 380 is secured in an engaged configuration, the occluder 310 is secured against axial motion with respect to the delivery wire 380. Thus, the occluder 310 is secured during delivery and the controlled motion of the collet sheath 350/collet tube 348 and the delivery wire 380 can deploy the occluder 310.

As illustrated in FIG. 22, the delivery wire 380 is threaded into the first securement system 330 by a threaded connection. As illustrated in FIG. 22, the female threads can be disposed on the delivery wire 380 and the male threads can be disposed on the occluder 310. FIG. 24 illustrates an alternative embodiment of a first securement system, designated 390, in which the male threaded portion 392 is disposed on the delivery wire 380 and the female threaded portion 394 is disposed on the occluder 310.

In a presently preferred embodiment, the male threads are disposed on the occluder 310 and the female threads are disposed on the delivery wire 380. This configuration has several advantages. First, the occluder 310 does not need a female connector and there is no cavity in which blood can stagnate and promote clotting. Second, the space required for the threaded connector 392 on the occluder 310 is diminished. Finally, a female connector on the delivery wire 380 may allow for a more smooth deployment of the occluder 310.

The first securement system interconnects the delivery wire 380 to the threaded portion on the occluder 310. Representative embodiments of the first securement system and its components are illustrated in more detail in FIGS. 23 and 24. In FIG. 23, the threaded portion 386, interconnects the delivery wire 380 and the threaded portion 332 on the occluder 310, illustrated in FIG. 20.

Referring again to FIG. 23, the delivery wire 380 has a more rigid section 382 and a more flexible section 384. In general, the flexible section 384 is distal to the more rigid section and is provided on the delivery end of the delivery wire 380. The delivery wire 380 can be any kind of flexible elongate member such as a wire, tube, hypotube, coil, or other hollow or solid constructions. The delivery wire 380 can be made from any material suitable for medical applications. Exemplary materials include metals and alloys suitable for medical applications, including stainless steel (such as "304 Stainless") and MP35N, polymers (such as nitinol), or any other suitable materials. The variation of stiffness can be the result of annealing; other material treatment process, or it may be a result of different materials being joined together. The amount of flexibility, or rigidity, can vary depending on the type of occluder being delivered and the delivery location within the body. The length of the flexible section 384 would typically be about the length of the occluder 310 in its delivery configuration. That is, the occluder 310 in the delivery configuration would surround the flexible portion of the delivery wire 380. The length of the flexible section 384, however, can be varied. The distal end of the delivery wire 380 includes a threaded attachment portion 386 on the end of the flexible section 384, described in detail below. The threaded portion 386 is illustrated as a female thread.

Figure 25A:
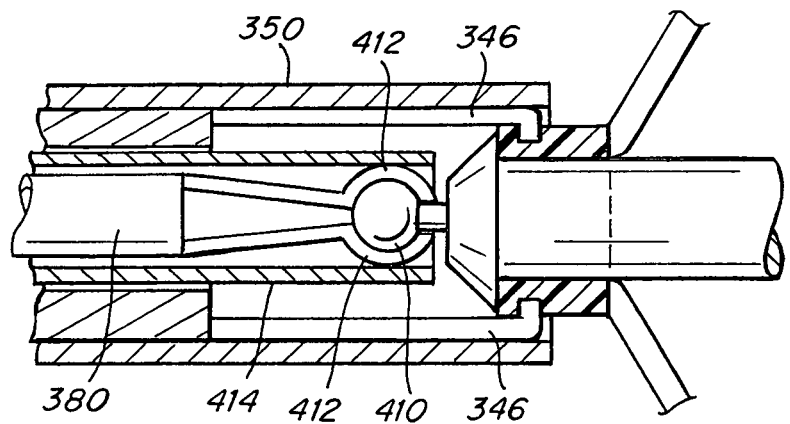
FIGS. 25A, 25B, 26A, 26B, 27A and 27B are alternative configurations for the first securement system according to aspects of the disclosure.
Figure 25B:
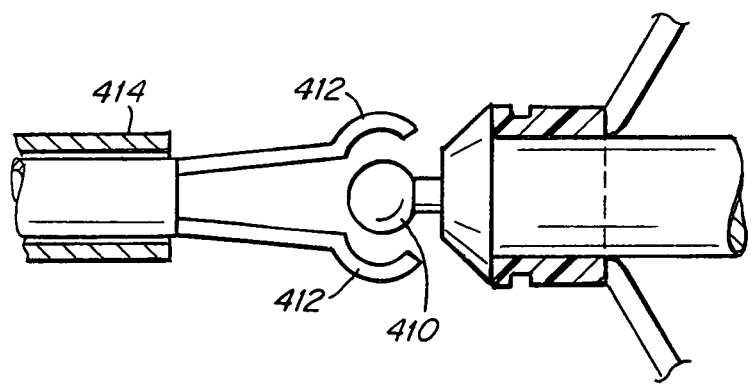

FIGS. 25A, 25B, 26A, 26B, 27A, and 27B illustrate alternative embodiments of the first securement system 330. Generically, all of the securement embodiments described can be properly described as interlocking systems. Each of these embodiments of the first securement system can be used with the threaded or collet connection for the second securement system and provide alternatives which may be appropriate for different kinds of occluding devices or other devices that could be delivered by the delivery system described in this application FIGS. 25A and 25B illustrate a ball and claw type attachment. In place of a screw type attachment, a ball 410 is disposed on the occluder and two or more claws 412 are sized to secure the ball 410 within the claws 412. The claws 412 are disposed at the distal end of the delivery wire 380. Two claws 412 are illustrated in FIG. 25B. The claws 412 operate under a similar principle as the collet design described previously. Specifically, there is a claw sheath 414 that is axially movable with respect to the claws 412. As illustrated in FIG. 25B the claws 412 splay out in the at rest configuration. When the claws 412 are in the claw sheath 414, the claws 412 are sized to secure the ball 410. Thus the configuration allows for a secure placement of the occluder on the delivery system. When the occluder is ready to be released claw sheath 414 is withdrawn and the claws 412 splay out to the at rest configuration. Thus the occluder is released from the first securement system.

Figure 26A:
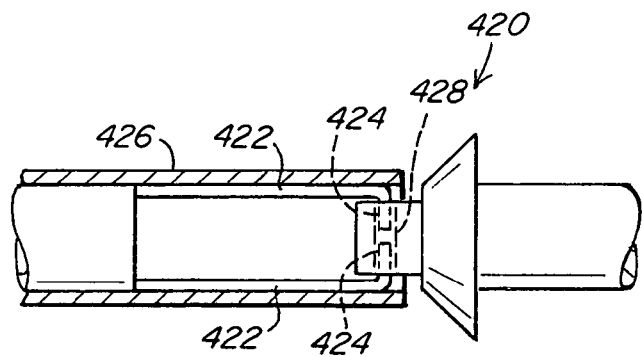
Figure 26B:
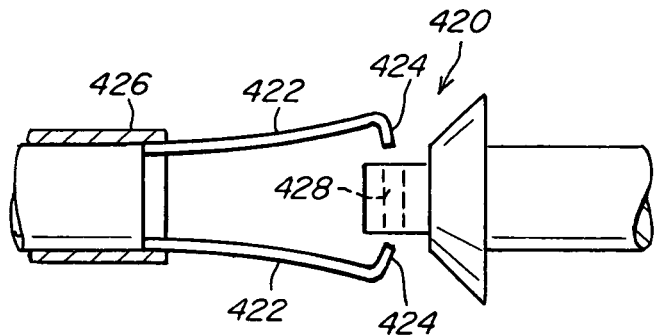

FIGS. 26A and 26B illustrate a pin-through-hole connector 420. In this embodiment, fingers 422 includes pins 424 that are disposed in an aperture in the occluder. As the example illustrates, the transverse aperture 428 is formed in the occluder and the transverse aperture 428 is sized to receive the pins 424. When the fingers 422 including pins 424 are in a sheath 426, the pins 424 are secured within the transverse aperture 428. Thus the configuration allows for a secure placement of the occluder on the delivery system. When the occluder is ready to be released a sheath 426 is withdrawn and the pins 424 spring back to the unbiased position similar to the fingers in the collet system. Thus the occluder is released from the first securement system.

Figure 27A:
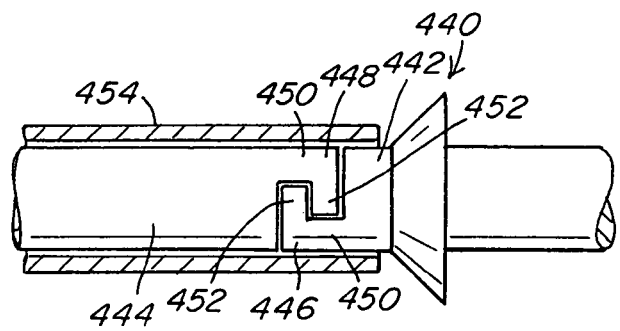
Figure 27B:
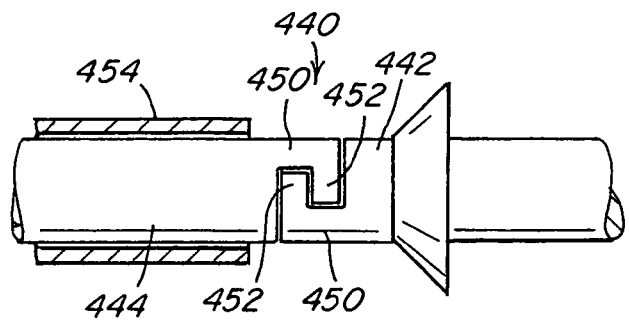

In another embodiment of the first securement system, illustrated in FIGS. 27A and 27B, a pair of cooperating configurations are secured when disposed within a sheath and separable when the sheath is withdrawn. This is a type of interlocking system 440. In this example, the lock is achieved using a combination of two C-shaped elements. Specifically, as illustrated, the occluder has a portion 442 that extends in an axial direction and is adapted to mate with a delivery wire 444. The portion 442 and the delivery wire 444 have cooperating extensions 446, 448 respectively that are able to interlock as illustrated in FIG. 27A. The system as illustrated has an interlocking elbow/arm attachment 450, 452 on each of the protrusion and the delivery wire. A variety of interlocking configurations are possible and the concept should not be limited to the configuration illustrated. When the interlocking system is disposed within a sheath 454, the cooperating extension cannot move with respect to each other. Thus the configuration allows for a secure placement of the occluder on the delivery system. When the cooperating extensions are extended beyond the sheath 454, the interlocking system can release and the occluder is released from the first securement system.

Figure 28:
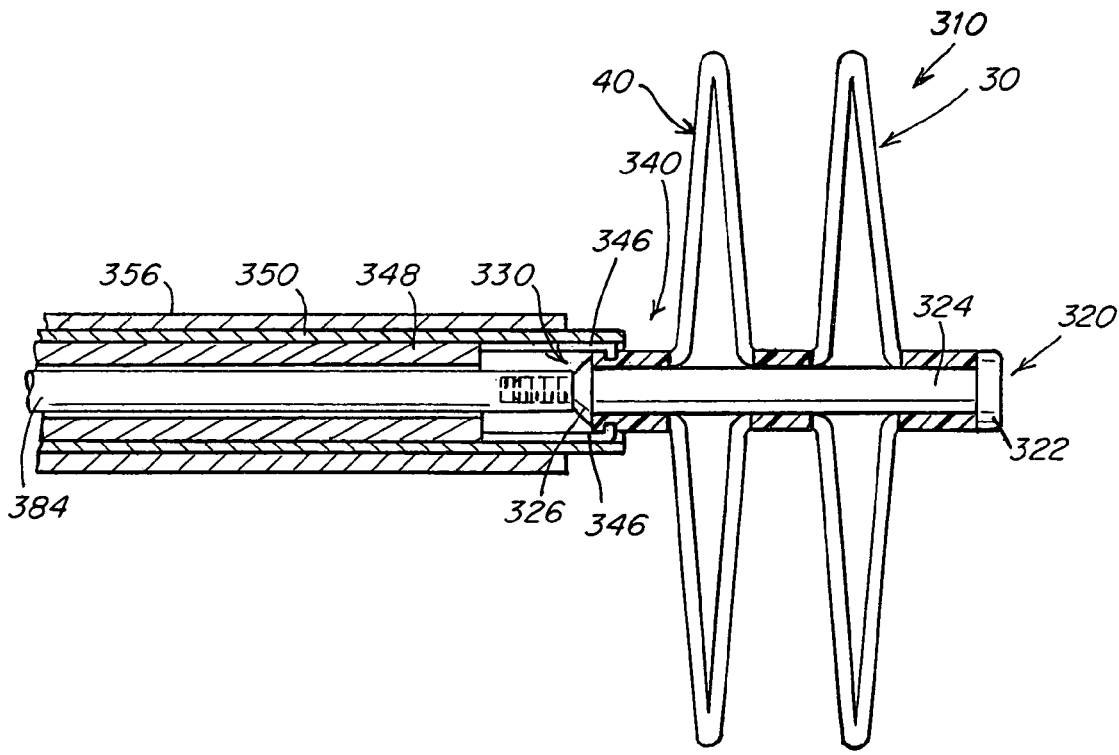
FIGS. 28 and 29 are detail cross-sectional side view of the delivery system during two steps in the deployment process according to one aspect of the disclosure.
Figure 29:
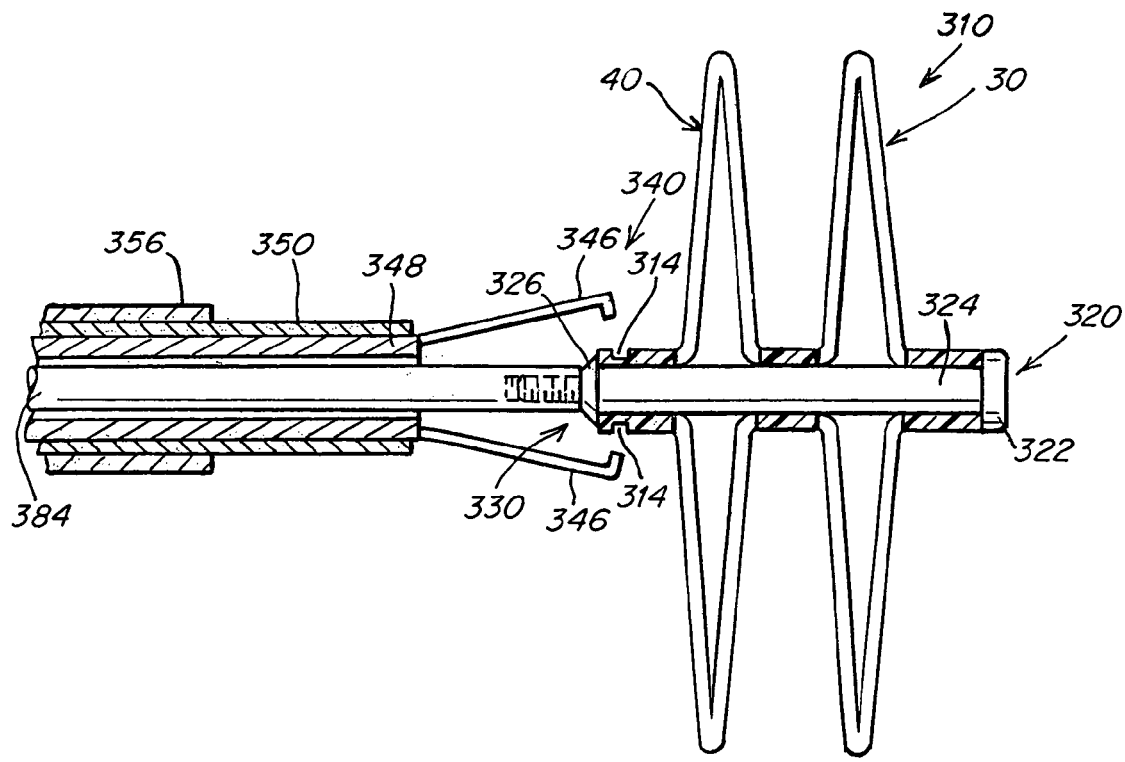

Any of the previous embodiments described in FIGS. 20-27B can be deployed in a manned illustrated in FIGS. 28 and 29. FIG. 28 illustrates the occluder 310 in its deployed configuration. To deploy the occluder 310, the delivery sheath 356 is withdrawn to expose the distal side loops 30 and then the proximal side loops 40 into the defect to be occluded. During this time the catch element 326 is engaged so that the occluder 310 is secured in the deployed configuration. Once the occluder 310 is in the deployed configuration the collet sheath 350 is withdrawn and the collet fingers 346 are unconstrained by the collet sheath 350 and are allowed to move radially outward to the unbiased condition, as illustrated in FIG. 29. Once the collet fingers 346 move radially outward the tips of the collet fingers 346 move away from the groove 314 in the occluder 310. Accordingly, the occluder 310 is only attached to the delivery by the first securement system 330. In this position, the clinician is able to evaluate the position of the occluder 310 to make sure that the device is properly positioned.

The process of retrieving an occluder varies based on the state of the delivery when the decision to retrieve the occluder is made. If the second and first securement systems are still attached and the catch system has not secured the device in the deployed configuration, then the retrieval process is simply a reversal of the deployment process. The second securement system is pulled and the device can be withdrawn into delivery sheath 356 and removed from the body.

If the catch system has secured the device in a deployed configuration, and the second and first securement systems are still attached, the process is the same with the addition of moving the catch element of the occluder relative to the second securement so that the device can be elongated. Once that occurs, the device can be withdrawn as described above.

The retrieval process for an occluder in which the second securement system is a collet system, which has been disengaged, requires an additional step. The collet system is advanced until the collet fingers are in alignment with the groove on the occluder. Next the collet sheath is advanced over the collet fingers such that the fingertips fit within the groove on the occluder. By pulling on the collet tube with the occluder firmly secured, the device can be returned to its collapsed state and retrieved into the delivery assembly. From this point the delivery process can be restarted.

Figure 30:
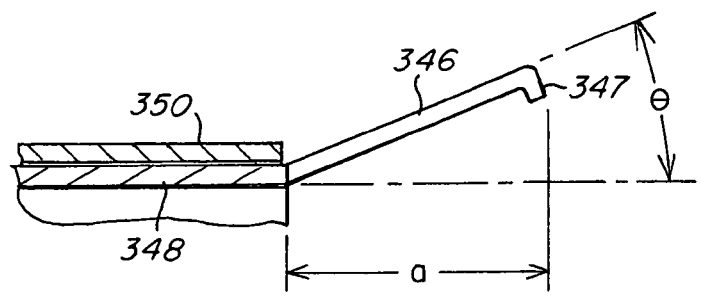
FIG. 30 is a detail view of the collet finger according to one aspect of the disclosure.

FIG. 30 illustrates a detail view of a collet finger 346 and the collet sheath 350. The collet finger 346 is configured to be about 20 degrees from the base of the collet finger 346, the dimension identified as θ in FIG. 30. The collet finger 346 can extend from the collet tube 348 approximately 0.25 in., the dimension identified as "a" in FIG. 30. The distance "a" can be from 0.1 in. to 0.5 in. The angle θ can vary from low single digits to approximately 70 degrees. In general, as the length of "a" is decreased, the angle desired for θ would increase. The collet finger 346 includes a radially inwardly extending protrusion 347, which is formed by a bend in the nitinol finger. The bend is preferably 90 degrees and the dimensions of the protrusion are selected to securely fit within the groove 314. As illustrated in FIG. 20, supra, the groove 314, for example, could be 0.02-0.04 in. in axial length and 0.005-0.020 in radial depth. The groove 314 is illustrated as a circumferential groove; alternatively, recesses can be formed in part of the occluder 310 to receive the collet fingers 346. It is preferable that the collet fingers 346 have a close fit but not an interference fit in the axial direction. This assures that the collet system can move the device without significant slippage. It is also preferable that the protrusion does not come into contact with the bottom of the groove 314 (the inner-most radial surface). This assists the deployment of the occluder.

Figure 31:
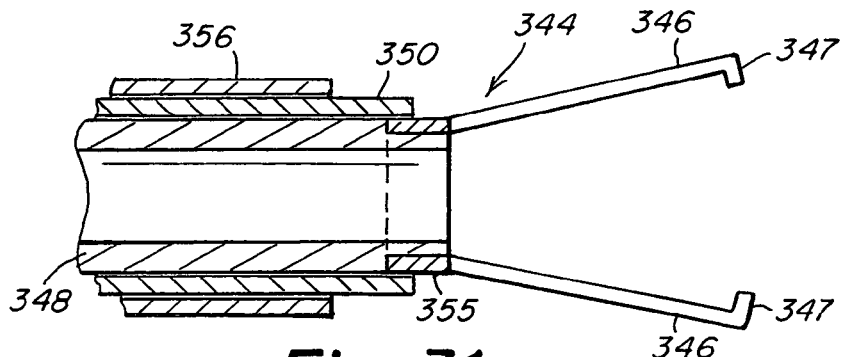
FIG. 31 is a detail cross-sectional side view of the collet system in the splayed configuration.
Figure 32A:
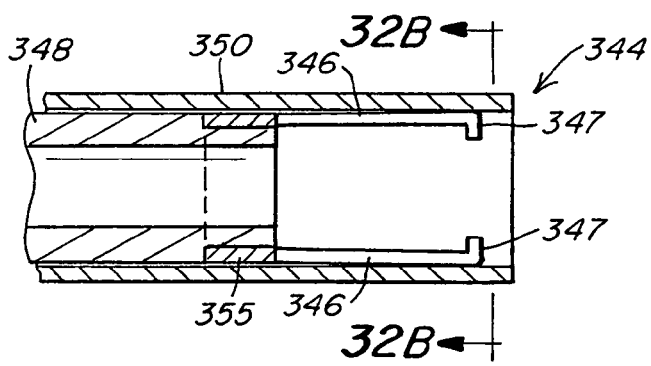
FIG. 32A is a detail cross-sectional view of the collet system in the constrained configuration.
Figure 32B:
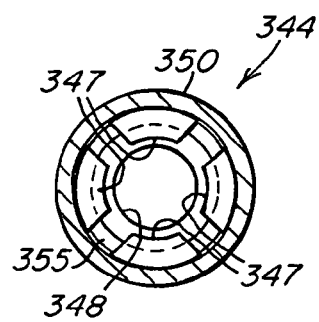
FIG. 32B is a cross-section taken along lines 32B-32B in FIG. 32A.

FIGS. 31, 32A, and 32B illustrate alternative embodiments of the second securement system. The fingers are formed by cutting sections from a nitinol hypotube that has, for example, a 0.0075 in. wall thickness. The inner diameter could be, for example, 0.098 in. and the outer diameter could be 0.117 in. The thickness of the hypotube could be as large as 0.050 in. or more. Nitinol is a desirable material due to its superelastic characteristics. Other superelastic materials or simply springy material may be used. Of course, the materials would have to be suitable for use in a medical device. The nitinol hypotube is cut so that the fingers extend from one side and the hypotube ring is uncut at the other end. As an example, FIG. 31 illustrates a cross section where the hypotube is disposed on an end of the collet tube 348. The nitinol ring 355 is disposed on the outside surface of the collet tube. The nitinol ring 355 may be affixed to the collet tube 348 by a variety of known techniques such as a suitable adhesive.

FIGS. 32A and 32B illustrate the side and end view of representative collet fingers 346. In a preferred embodiment, there are four collet fingers 346 that are used to secure the occluder in the delivery system. In alternate embodiments, there may be as few as two collet fingers 346 or as many as 8. One practical limitation is the circumferential size of the collet fingers 346 and the rigidity of the collet fingers 346 as they are used to deploy the occluder. In the embodiment illustrated in FIG. 32B, the four collet fingers 346 are formed by cutting away a $\frac{1}{8}^{th}$ section of the cross section and forming four equally spaced collect fingers 346. During the formation process the roundness of the collet finger 346 along the circumference can be modified to adjust the bendability of the collet fingers 346.

Figure 33:
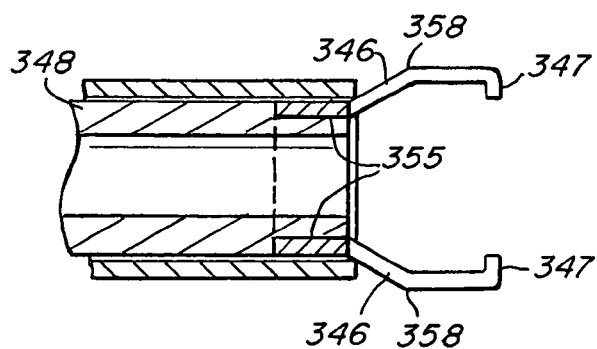
FIG. 33 is a detail sectional view of another embodiment of the collet system according to the disclosure.

FIG. 33 illustrates another embodiment of the collet fingers 346. In this embodiment, the collet fingers 346 include a bend 358 between the base ring 355 and the protrusion 347. As illustrated the bend 358 is in the approximate halfway between the base ring 355 and the protrusion 347. The bend 358 can be almost any configuration but the bend 358, as illustrated, allows for force to be applied to the occluder and have the configuration of the collet fingers 346 be such that it does not extend the so far away from the collet tube 348 in the radial direction. This allows the occluder to have a more controlled delivery because of the increased forces applied and a more compact system because the collet fingers 346 do not extend radially away from the collet tube 348 as far.

Figure 34:
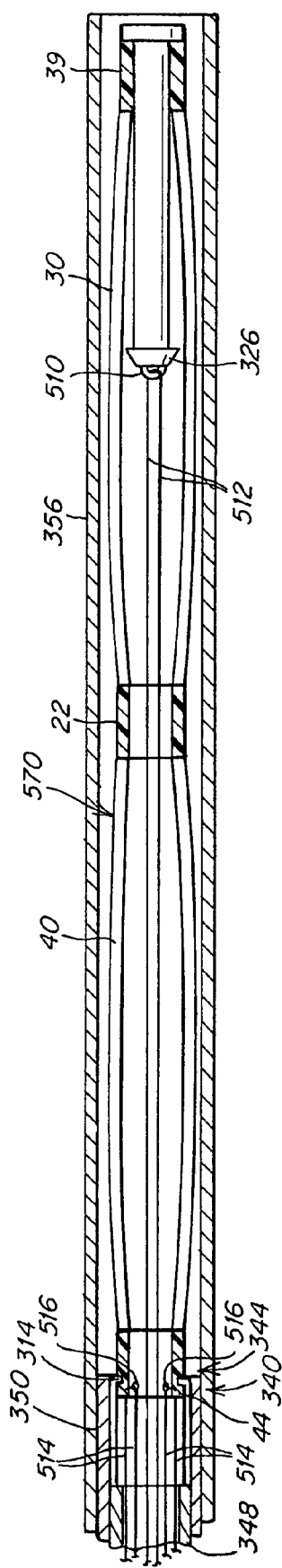
FIGS. 34-37 are sectional views of an alternative delivery system according to an aspect of the disclosure.

Another embodiment of the second and first securement system of the delivery system, illustrated in FIGS. 34-37, uses a filament instead of a delivery wire. As shown in FIG. 34, the second securement system 340 is illustrated as the collet system 344, which is largely the same as in the previous embodiment. Of course, other securement systems included a threaded connection can be used. The first securement system includes an eyelet 510 around which a flexible filament 512 can be fastened or looped. The flexible filament can be a suture thread (monofilament or polyfilament), a thin metallic wire or other flexible material that can withstand a tension load.

Figure 35:
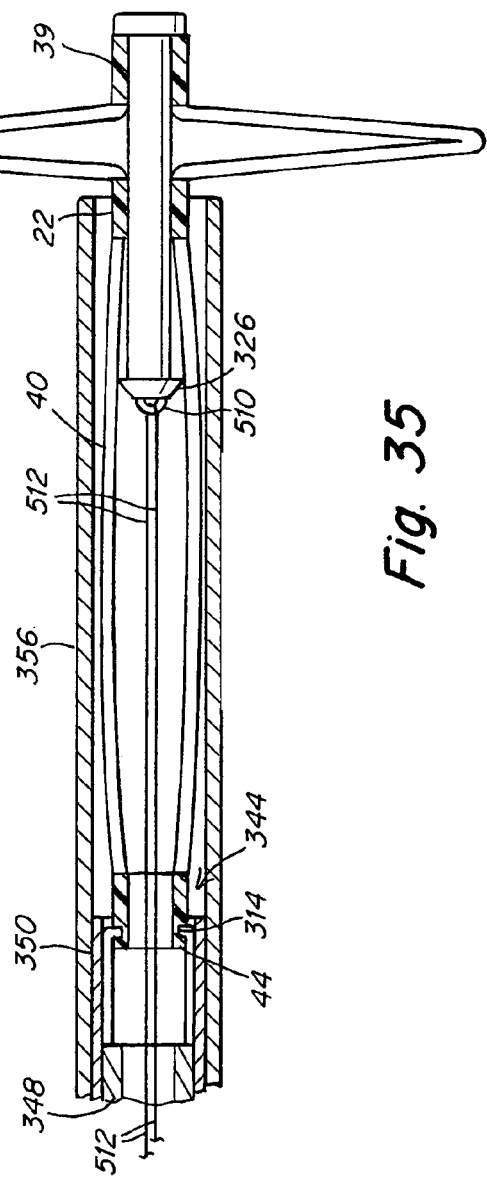
Figure 36:
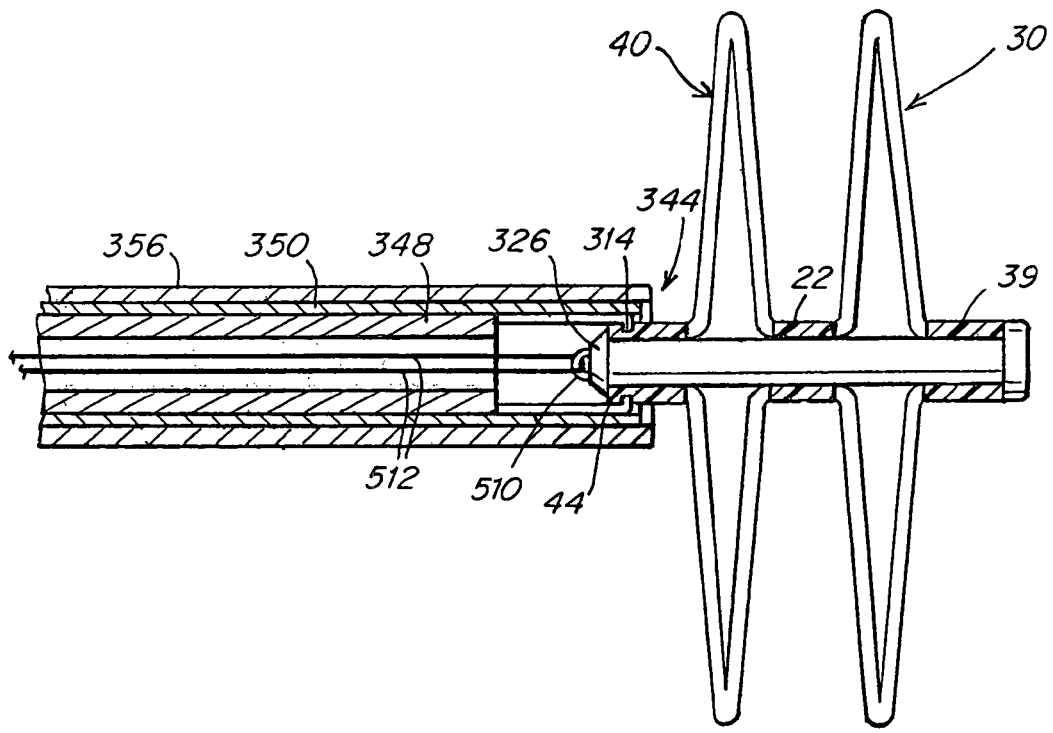
Figure 37:
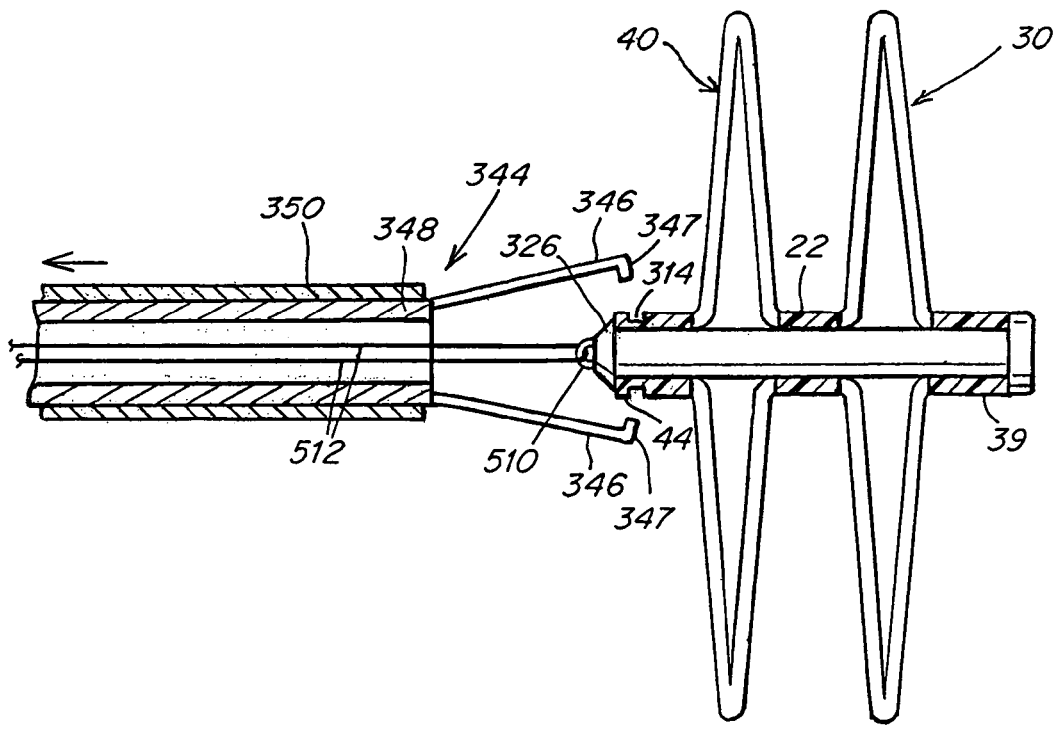

The deployment of the occluder is effected by withdrawing the delivery sheath 356 to expose and let the distal petals 30 on the distal side of the occluder expand as illustrated in FIG. 35. Once the distal petals 30 are deployed by the catch element 326, the delivery sheath 356 is repositioned to the deployment site of the proximal petals 40 and the proximal petals 40 are exposed as illustrated in FIG. 36. The filament is pulled to cause the catch element at the proximal side of the occluder to be secured. Once the catch element secures the occluder in the deployed configuration, the collet system is released in the manner described above and illustrated in FIG. 37. Once the collet system is released, the position may be evaluated. If the position is satisfactory, filament 510 is pulled through the eyelet and removed from the body. Either a delivery wire, a tube or filament is appropriate for the second securement system depending on the design considerations. For example, if the occluder in the delivery configuration lacks sufficient column strength to have the delivery sheath pull back without affecting the position of the device in the delivery system, a delivery wire that has some column strength would be more desirable.

An alternative recovery sequence is also provided. The recovery process for a device in which the second securement (e.g., collet) system has been disengaged, the process requires an additional step. For systems in which a retrieval capability is desired, additional filaments can be attached to the proximal tip of the occluder. For example, with reference to FIG. 34, filaments 514 are attached to the proximal end 44 of the occluder 570 through holes 516. The filaments 514 can be attached in a variety of locations, for example, they can be looped around one of the proximal loops on the proximal side of the device. When the filaments 514 are provided, the clinician would orient the delivery catheter 548 (as illustrated in FIG. 38B) to the proximal end 44 of the occluder 570 and then pull on the filaments 514 to uncatch the system so that the profile of the device can be reduced and reinserted into the delivery catheter. In an embodiment where the filament 514 is present and the device is deployed satisfactorily, the filaments 514 can be cut or otherwise withdrawn from the body.

Figure 38A:
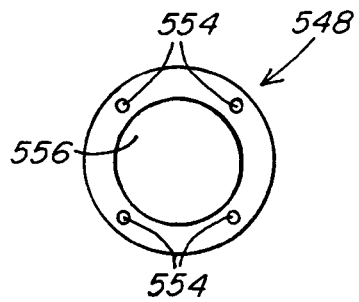
FIG. 38A is a front cross-sectional view of a delivery catheter according to one embodiment of the disclosure.
Figure 38B:
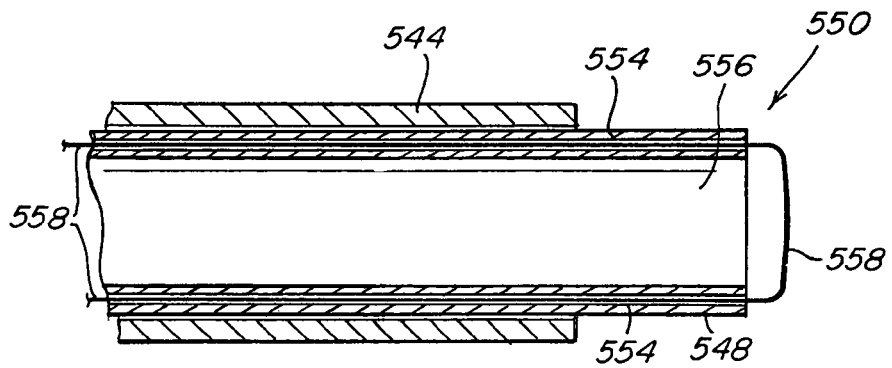
FIG. 38B is a side cross-sectional view of a delivery catheter with sutures according to one embodiment of the disclosure.
Figure 38C:
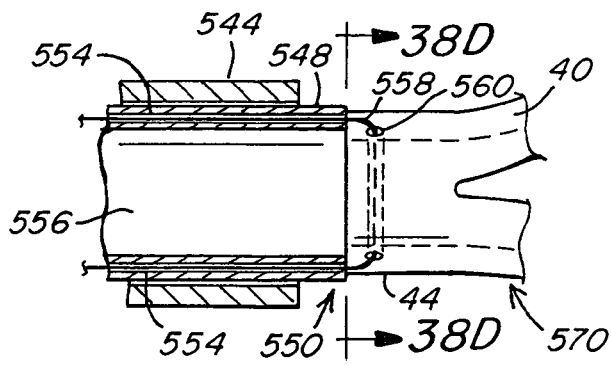
FIG. 38C is a side cross-sectional view of a delivery catheter with sutures secured to an occluder according to one embodiment of the disclosure.
Figure 38D:
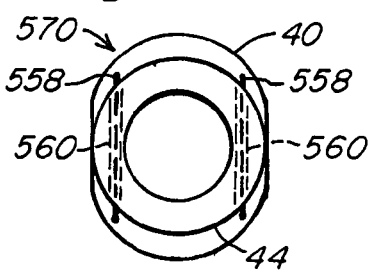
FIG. 38D is an elevational end view of delivery catheter along lines 38D of FIG. 38C.

FIG. 38A illustrates an end view of the construction of the delivery catheter 548. The delivery catheter 548 a central lumen 556 and secondary lumens 554 surrounding the central lumen 556. The outer lumens 554 are used to provide a passageway for containing sutures 558 secured to the occluder 570, illustrated in FIG. 38C, as the attachment mechanism for the second securement system 340 and passed through the delivery catheter 548 to the user for manipulating the second securement system. Although four outer lumens 554 are shown, any number of lumens may be provided suitable for use in the delivery system 340. A sufficient number of sutures 558 should be provided in order to securely attach the occluder 570 and permit the necessary operations. The sutures 558 are shown in FIG. 38B, which illustrates delivery sheath 544 which contains delivery catheter 548. Referring again to FIG. 38C, the delivery catheter 548 is connected to the proximal end 44 of the occluder 570 via the sutures 558 which attach to holes 560 provided in the occluder 570. The sutures 558 are threaded through the holes 560 and can be readily detached by, e.g., cutting the sutures and pulling through the delivery catheter 548. Attachment of the sutures 558 to the occluder 570 may be provided in a number of ways, such as providing hooks or a flange on the occluder 570, around which the sutures can be wrapped or fastened, or wrapping the sutures 558 around the proximal petals 42. The sutures 558 can also be embedded into the proximal end 44 of the occluder 570. The flexible filament used to provide the thread can be a suture thread (monofilament or polyfilament), a thin metallic wire or other flexible material that can withstand a tension load.

Figure 39:
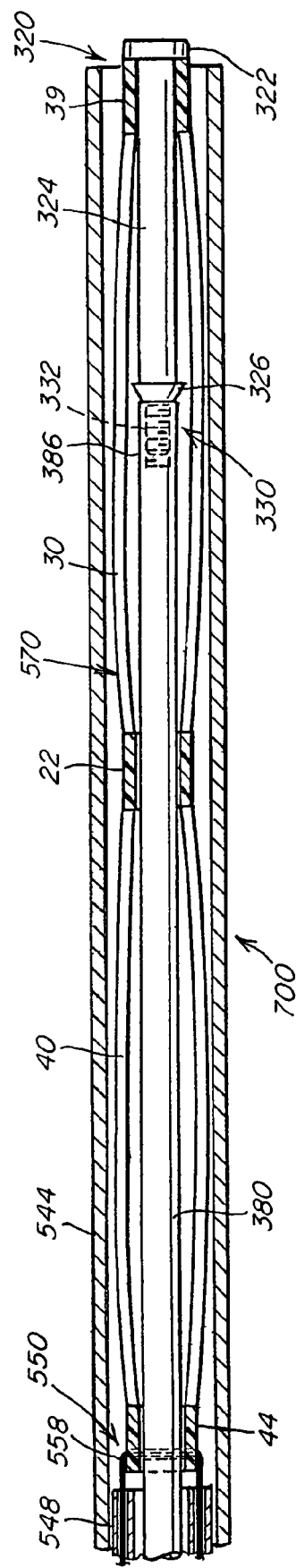
FIG. 39 is a sectional view of a delivery assembly during a step in the deployment process according to one aspect of the disclosure.

FIG. 39 illustrates a complete delivery assembly 700 with the occluder 570 in place for delivery and deployment at the deployment site. As shown, the occluder 570 is in its elongated, low profile configuration. The occluder 570 is secured at its distal end 39 by the first securement system 330 to the delivery wire 380 and at its proximal end 44 by the second securement system 550 to the delivery catheter 548. The occluder 570, delivery wire 380 and delivery catheter 548 are contained within the sheath 544. The occluder 570 can be detached from the first securement system 380 by unscrewing the delivery wire 330, which is connected by threaded portion 386 to threaded portion 332. The occluder 570 can be detached from the second securement system 550 by removing the sutures 558, for example, by pulling on them from the user end of the delivery system.

The embodiments and techniques described here are described preferably for use with a device made of a polymer and formed from a single tube, such that the tube is a single monolithic material. The catch mechanism can be all or partly monolithic or integral with the tubular structure, or there can be an absence of any type of bonding or rigid connection to the rest of the tubular structure, in which case there may be some spring force or other force that holds the locking mechanism in place. While the device is thus shown as being substantially formed from a single tubular body, the catch mechanism as described in the embodiments above could be used with other types of devices, including those formed from many pieces, and including devices formed from other materials, including metals, polymers, stainless steel or nitinol.

The term "bioabsorbable," as used in the description above, is also understood to mean "bioresorbable."

While the description above refers to strings, filaments, sutures and wires, and while the term "wire" might convey a more rigid piece than a string, a suture or a filament, all these terms are essentially interchangeable, and further include embodiments in which the wire, string, suture or filament is a hollow tube or conduit to allow another wire, as needed, to pass through its longitudinal axis. Each wire, string, suture and filament can be composed of one or more wires, strings, sutures and filaments.

In cases in which the device is made of a polymer, it can be desirable to add an additive or coating to the material to make it radiopaque to make it more visible in a wider variety of imaging techniques.

It will be appreciated that while a particular sequence of steps has been shown and described for purposes of explanation, the sequence may be varied in certain respects, or the steps may be combined, while still obtaining the desired deployment or in some cases to effect deployment in a particular way. For example, the delivery sheath may be advanced or retracted at varying times and in varying degrees, the proximal and distal portions of the occluder may be deployed into the petal configuration in a different sequence, etc. In addition, the steps could be automated.

The invention claimed is:

1. A medical apparatus including a collapsible for occluding an aperture in a body, the medical device having a first configuration as a reduced profile and a second configuration as an expanded profile, the medical device being adapted to be delivered into a desired delivery location through a delivery system comprising a delivery wire and a delivery catheter, the medical device comprising:
a proximal side and a distal side,
a first threaded portion directly coupling the proximal side of the device to a threaded portion of the delivery catheter of the delivery system, and a second threaded portion directly coupling the distal side of the device to a threaded portion of the delivery wire of the delivery system wherein the relative cooperative movement of the first threaded portion and the second threaded portion changes the configuration of the device from the expanded profile configuration to the reduced profile, and wherein the first threaded portion and the second threaded portion are positioned on the proximal side of the device when the device is in the expanded profile configuration.

2. A medical apparatus including a medical device for occluding an aperture in a body and a delivery system comprising a delivery wire and a delivery catheter, the medical device having a first configuration as a reduced profile and a second configuration as an expanded profile, the medical device being adapted to be delivered through the delivery system into a desired delivery location, the medical device comprising:

a tube comprising a proximal side and a distal side, a central portion disposed between the proximal side and the distal side of the tube, the central portion remaining disposed along a central axis of the device when an axial length of the tube is shortened, the proximal and distal sides comprising an arrangement of struts, whereby loops having a first and second end are formed from the struts by the axial shortening of the tube and each loop originates at a first end from the central portion of the tube;

a first attachment securing the device to the delivery system, the first attachment being disposed at a central axis of the device and including a threaded connection directly coupling the device to the delivery wire of the delivery system, and a second attachment securing the device to the delivery system, the second attachment including a threaded connection with male threads disposed on a surface of the device directly coupling the device to the delivery catheter of the delivery system wherein the relative movement of the second attachment and the first attachment when the first attachment and second attachment are coupled to the delivery system shortens the axial length of the tube to change the configuration of the device from the reduced profile configuration to the expanded profile configuration so the loops extend radially from the central axis of the device, wherein both the first attachment and second attachments are releasable by unscrewing the threaded connection, and wherein the threaded connection of the first attachment and the threaded connection of the second attachment are positioned proximal to the arrangement of struts of the proximal side when the device is in the expanded profile.

3. The medical apparatus recited in claim 2, wherein threads associated with the first attachment are configured to be unscrewed with a different rotational direction than threads associated with the second attachment.

4. The medical apparatus recited in claim 2, wherein threads associated with the first attachment are configured to be unscrewed with the same rotational direction as threads associated with the second attachment.

5. The medical apparatus recited in claim 2, wherein the medical device is bioabsorbable.

* * * * *